US011899019B2

(12) United States Patent
Endou et al.

(10) Patent No.: US 11,899,019 B2
(45) Date of Patent: Feb. 13, 2024

(54) METHOD FOR PREDICTING EFFICACY OF ANTI-PD-1 ANTIBODY OR ANTI-PD-L1 ANTIBODY THERAPY, METHOD FOR EVALUATING CANCER GRADE, AND METHOD FOR ENHANCING EFFICACY OF ANTI-PD-1 ANTIBODY OR ANTI-PD-L1 ANTIBODY THERAPY

(71) Applicants: J-Pharma Co., Ltd., Yokohama (JP); NATIONAL UNIVERSITY CORPORATION GUNMA UNIVERSITY, Maebashi (JP); OSAKA UNIVERSITY, Suita (JP)

(72) Inventors: Hitoshi Endou, Yokohama (JP); Goshi Ishihara, Yokohama (JP); Kyoichi Kaira, Hidaka (JP); Yoshikatsu Kanai, Suita (JP)

(73) Assignees: J-PHARMA CO., LTD., Yokohama (JP); NATIONAL UNIVERSITY CORPORATION GUNMA UNIVERSITY, Maebashi (JP); OSAKA UNIVERSITY, Suita (JP)

( * ) Notice: Subject to any disclaimer, the term of this patent is extended or adjusted under 35 U.S.C. 154(b) by 558 days.

(21) Appl. No.: 16/623,573

(22) PCT Filed: Nov. 7, 2018

(86) PCT No.: PCT/JP2018/041380
§ 371 (c)(1),
(2) Date: Dec. 17, 2019

(87) PCT Pub. No.: WO2019/093383
PCT Pub. Date: May 16, 2019

(65) Prior Publication Data
US 2021/0148920 A1    May 20, 2021

(30) Foreign Application Priority Data
Nov. 7, 2017   (JP) .................................. 2017-214936

(51) Int. Cl.
C07K 16/28     (2006.01)
A61K 39/395    (2006.01)
A61K 31/423    (2006.01)
A61P 35/00     (2006.01)
G01N 33/68     (2006.01)

(52) U.S. Cl.
CPC ......... *G01N 33/68* (2013.01); *C07K 16/2818* (2013.01); *C07K 16/2827* (2013.01); *G01N 2800/52* (2013.01)

(58) Field of Classification Search
None
See application file for complete search history.

(56) References Cited

U.S. PATENT DOCUMENTS

| 7,595,048 B2 * | 9/2009 | Honjo ..................... A61P 31/18 |
| | | 424/142.1 |
| 10,172,835 B2 * | 1/2019 | Endou ..................... A61P 35/00 |
| 2011/0020370 A1 * | 1/2011 | Georges .................. A61P 25/00 |
| | | 424/277.1 |
| 2016/0279103 A1 * | 9/2016 | Endou .................. A61K 33/243 |
| 2020/0121803 A1 * | 4/2020 | Benatuil .............. A61K 31/495 |
| 2020/0405695 A1 * | 12/2020 | Endou ..................... A61P 35/00 |
| 2022/0288035 A1 * | 9/2022 | Yoshitake .............. A61K 45/06 |
| 2022/0288036 A1 * | 9/2022 | Yoshitake ............ C12Q 1/6886 |

FOREIGN PATENT DOCUMENTS

| CN | 105392498 A | 3/2016 |
| KR | 10-2017-0027852 A | 3/2017 |
| WO | 2015/173970 A1 | 11/2015 |
| WO | 2017/214462 A2 | 12/2017 |

OTHER PUBLICATIONS

Kim et al. (2016) Immune escape to PD-L1/PD-1 blockade: seven steps to success (or failure). Annals of Oncology 27: 1492-1504.*
Parks et al. (2017) Hypoxia and cellular metabolism in tumour pathophysiology. J Physiol. 595.8: 2439-2450.*
Yun et al. (2014) JPH203, an L-type amino acid transporter 1-selective compound, induces apoptosis of YD-38 human oral cancer cells. J Pharmacol Sci 124: 208-217.*
Oda et al. (2010) L-type amino acid transporter 1 inhibitors inhibit tumor cell growth. Cancer Sci 101: 173-179.*

(Continued)

*Primary Examiner* — Ilia I Ouspenski
(74) *Attorney, Agent, or Firm* — WHDA, LLP

(57) ABSTRACT

Methods are provided for predicting a response to an anti-PD-1 antibody or anti-PD-L1 antibody therapy based on a new biomarker and for evaluating a malignancy of cancer. The method for predicting a response of a subject to an anti-PD-1 antibody or anti-PD-L1 antibody therapy includes measuring an expression level of LAT1 in a sample collected from a cancer tissue of the subject; and predicting a response of the subject to the anti-PD-1 antibody or anti-PD-L1 antibody therapy based on the expression level of LAT1. The method for evaluating a malignancy of cancer in a subject includes staining a sample collected from a cancer tissue of the subject with an anti-LAT1 antibody and an anti-PD-L1 antibody; and evaluating a malignancy of the cancer in the subject based on a presence or absence of a LAT1-positive and PD-L1-positive site.

1 Claim, 16 Drawing Sheets

Specification includes a Sequence Listing.

(56) References Cited

OTHER PUBLICATIONS

Imai et al. (2010) Inhibition of L-type amino acid transporter 1 has antitumor activity in non-small cell lung cancer. Anticancer Res 30: 4819-4828.*
Ohshima et al. (2016) Efficacy of system I amino acid transporter 1 inhibition as a therapeutic target in esophageal squamous cell carcinoma. Cancer Science 107.10: 1499-1505.*
Rosilio et al. (2015) L-type amino-acid transporter 1 (LAT1): a therapeutic target supporting growth and survival of T-cell lymphoblastic lymphoma/T-cell acute lymphoblastic leukemia. Leukemia 29.6: 1253-1266.*
Cormerais et al. (2016) Genetic Disruption of the Multifunctional CD98/LAT1 Complex Demonstrates the Key Role of Essential Amino Acid Transport in the Control of mTORC1 and Tumor Growth. Cancer Research 76.15: 4481-4492.*
Yothaisong et al. (2017) Inhibition of I-type amino acid transporter 1 activity as a new therapeutic target for cholangiocarcinoma treatment. Tumor Biology 39.3 (14 pages).*
Hayes et al. (2015) Int. J. Cancer 137: 710-720.*
Kurihara et al. (2015) PLoS ONE 10(10): e0139692; 1-13.*
Cantor et al. (2012) Journal of Cell Science 125 (6): 1373-1382.*
Ip et al. (2016) Int. J Biochem. & Cell Biol. 81: 148-150.*
Kantipudi et al. (2020) Int. J. Mol. Sci. 21: 7573; 1-11 (provided by applicant).*
Napolitano et al. (2015) Int. J Biochem. & Cell Biol. 67: 25-33 (provided by applicant).*
Ueno, Seiji et al., "Metformin enhances anti-tumor effect of L-type amino acid transporter 1 (LAT1) inhibitor", Journal of Pharmacological Sciences, 2016, vol. 131, 2016, p. 110-p. 117; Cited in KR Office Action dated Jan. 4, 2021. (8 pages).
Kaira, Kyoichi et al., "Prognostic significance of L-type amino acid transporter 1 (LAT1) expression in patients with ovarian tumors", Am J Transl Res., 2015, vol. 7, 2015, p. 1161-p. 1171; Cited in KR Office Action dated Jan. 4, 2021. (11 pages).
E. Hogdall et al., "PD-L1 expression and prognosis significance in advanced ovarian cancer", Abstracts Gynaecological Cancers, (Sep. 2017), vol. 28, Supplement 5, 937PD., 2017; Cited in KR Office Action dated Jan. 4, 2021. (2 pages).
Honjo et al., "Basics and clinical application of cancer treatment with anti-PD-1 antibody (in Japanese)", 2013 Taiwan-Japan Science and Technology Forum, Development of Translational Medicine and Bioindustry, Sep. 23, 2013, with partial translation, cited in specification. (46 pages).
Kaira et al., "Prognostic significance of L-type amino acid transporter 1 expression in resectable stage I-III nonsmall cell lung cancer", British Journal of Cancer, 2008, vol. 98, No. 4, p. 742-p. 748, cited in specification. (7 pages).
Ichinoe et al., "High expression of L-type amino-acid transporter 1 (LAT1) in gastric carcinomas: Comparison with non-cancerous lesions", Pathology International, 2011, vol. 61, issue 5, p. 281-p. 289, cited in specification. (9 pages).
Yanagisawa et al., "High expression of L-type amino acid transporter 1 (LAT1) predicts poor prognosis in pancreatic ductal adenocarcinomas", Journal of Clinical Pathology, 2012, vol. 65, issue 11, cited in specification. (7 pages).
Yanagisawa et al., "High expression of L-type amino acid transporter 1 (LAT1) as a prognostic marker in bile duct adenocarcinomas", Cancer Medicine, 2014, vol. 3, issue 5, p. 1246-p. 1255, cited in specification. (10 pages).
Watanabe et al., "L-type Amino Acid Transporter 1 Expression Increases in Well-Differentiated but Decreases in Poorly Differentiated Endometrial Endometrioid Adenocarcinoma and Shows an Inverse Correlation With p53 Expression", International Journal of Gynecologic Cancer, 2014, vol. 24, issue 4, p. 659-p. 663, cited in specification. (5 pages).
Sakata et al., "L-type amino-acid transporter 1 as a novel biomarker for high-grade malignancy in prostate cancer", Pathology International, 2009, vol. 59, issue 1, p. 7-p. 18, cited in specification. (12 pages).
Kaira et al., "L-type amino acid transporter 1 and CD98 expression in primary and metastatic sites of human neoplasms", Cancer Science, 2008, vol. 99, issue 12, p. 2380-p. 2386, cited in specification. (7 pages).
Kaji, Masahiko et al., "Expression and physiological role of amino acid transporter LAT1 in ovarian malignant tumor", Acta obstetrica et gynaecologica Japonica, 2007, vol. 59, No. 2, p. 394, with English translation, cited in ISR dated Feb. 5, 2019. (2 pages).
Philips, G. K. et al., "Therapeutic uses of anti-PD-1 and anti-PD-L1 antibodies", International Immunology, Oct. 2014, vol. 27, No. 1, p. 39-p. 46, cited in ISR dated Feb. 5, 2019. (8 pages).
Oda, K. et al., "L-Type amino acid transporter 1 inhibitors inhibit tumor cell growth", Cancer Science, Jan. 2010, vol. 101, No. 1, p. 173-p. 179, cited in ISR dated Feb. 5, 2019. (7 pages).
Wempe, M. F. et al., "Metabolism and Pharmacokinetic Studies of JPH203, an L-Amino Acid Transporter 1 (LAT1) Selective Compound", Drug Metabolism and Pharmacokinetics, 2012, vol. 27, No. 1, p. 155-p. 161, cited in ISR dated Feb. 5, 2019. (7 pages).
Takeuchi, K. et al., "LAT1 expression in non-small-cell lung carcinomas: Analyses by semiquantitative reverse transcription-PCR (237 cases) and immunohistochemistry (295 cases)", Lung Cancer, 2010, vol. 68, p. 58-p. 65, cited in Feb. 5, 2019. (8 pages).
Das, R. et al., "Combination therapy with anti-CTLA4 and anti-PD1 leads to distinct immunologic changes in vivo", The Journal of Immunology, Feb. 2015, vol. 194, No. 3, p. 950-p. 959, cited in Feb. 5, 2019. (10 pages).
Emi Mashima et al., "Nivolumab in the treatment of malignant melanoma: review of the literature", OncoTargets and Therapy, 2015, vol. 8, p. 2045-p. 2051. (7 pages).
International Search Report dated Feb. 5, 2019, issued in counterpart application No. PCT/JP2018/041380. (2 pages).
Notification of Transmittal of Translation of the International Preliminary Report on Patentability (Forms PCT/IB/338) issued in counterpart International Application No. PCT/JP2018/041380 dated May 7, 2020 with Forms PCT/IPEA/409. (8 pages).
Yu, J. et al., "PD-L1 expression in human cancers and its association with clinical outcomes", OncoTargets and Therapy, Aug. 1, 2016, pp. 5023-5039, vol. 9, XP055486852, cited in Extended European Search Report dated Jun. 18, 2021. (17 pages).
Zhao, Y. et al., "The role of L-type amino acid transporter 1 in human tumors", Intractable & Rare Diseases Research, Jan. 1, 2015, pp. 165-169, vol. 4, No. 4, XP055812555, cited in Extended European Search Report dated Jun. 18, 2021. (5 pages).
Extended European Search Report dated Jun. 18, 2021, issued in counterpart EP Application No. 18876954.1. (8 pages).
Office Action dated Mar. 31, 2023, issued in counterpart CN Application No. 201880038920.9. (8 pages).

* cited by examiner (A)

(B)

(A)

(B)

(A)

(B)

(A)

(B)

(A)

(B)

METHOD FOR PREDICTING EFFICACY OF ANTI-PD-1 ANTIBODY OR ANTI-PD-L1 ANTIBODY THERAPY, METHOD FOR EVALUATING CANCER GRADE, AND METHOD FOR ENHANCING EFFICACY OF ANTI-PD-1 ANTIBODY OR ANTI-PD-L1 ANTIBODY THERAPY

TECHNICAL FIELD

The present invention relates to a method for predicting a response to an anti-PD-1 antibody or anti-PD-L1 antibody therapy, a method for evaluating a malignancy of cancer, and a method for increasing response to an anti-PD-1 antibody or anti-PD-L1 antibody therapy.

BACKGROUND ART

Agents targeting PD-1 (Programmed cell death 1)/PD-L1 (Programmed cell death ligand-1) have been developed as immune checkpoint inhibitors. For example, nivolumab and pembrolizumab have been developed as anti-PD-1 monoclonal antibodies and atezolizumab, avelumab, and durvalumab have been developed as anti-PD-L1 monoclonal antibodies. Moreover, methods for examining the PD-L1 expression in cancer cells in patients have been developed as methods for predicting a response to an anti-PD-1 antibody therapy.

An inverse correlation of the expression of PD-L1 with the prognoses of many cancers (kidney cancer, esophageal cancer, gastric cancer, urothelial carcinoma, pancreatic cancer, melanoma, and the like) has been observed (Non Patent Literature 1). However, correlation between the response rates of recent anti-PD-1 monoclonal antibody drugs or anti-PD-L1 monoclonal antibody drugs and the intensity of expression of the PD-L1 protein in cancer tissues of patients is not clear, and it is hard to say that the measurement of the intensity of PD-L1 expression plays a role as so-called companion diagnostics.

LAT1 (L-type amino acid transporter 1), which is expressed in cancer tissues, is one of carcinoembryonic proteins and the expression level thereof is high in cancer tissues with high malignancy (fatality rate). A strong correlation between the intensity of LAT1 expression and the fatality rate of patients has been reported in many cancers (lung cancer, Non Patent Literature 2; gastric cancer, Non Patent Literature 3; pancreatic cancer, Non Patent Literature 4; biliary cancer, Non Patent Literature 5; endometrial cancer, Non Patent Literature 6; prostate cancer, Non Patent Literature 7; colorectal cancer, mammary gland cancer, head and neck cancer, genital organ cancer and soft tissue cancer, Non Patent Literature 8).

CITATION LIST

Non Patent Literature

Non Patent Literature 1: Honjo et al., "Basics and clinical application of cancer treatment with anti-PD-1 antibody (in Japanese)", 2013 Taiwan-Japan Science and Technology Forum, Development of Translational Medicine and Bioindustry, Sep. 23, 2013, hftp://www.tnst.org.tw/ezcat-files/cust/img/img/20130923_jp11.pdf Non Patent Literature 2: Kaira et al., "Prognostic significance of L-type amino acid transporter 1 expression in resectable stage I-III nonsmall cell lung cancer.", Br J Cancer. 98(4):742-8, 2008.

Non Patent Literature 3: Ichinoe et al., "High expression of L-type amino-acid transporter 1 (LAT1) in gastric carcinomas: Comparison with non-cancerous lesions.", Pathol Int. 61(5):281-9, 2011.

Non Patent Literature 4: Yanagisawa et al. "High expression of L-type amino acid tansporter 1 (LAT1) predicts poor prognosis in pancreatic ductal adenocarcinomas.", J Clin Pathol. 65(11): 1019-23, 2012. Non Patent Literature 5: Yanagisawa et al, "High expression of L-type amino acid transporter 1 (LAT1) as a prognostic marker in bile duct adenocarcinomas.", Cancer Med. 3(5):1246-55, 2014.

Non Patent Literature 6: Watanabe et al., "L-type amino acid transporter 1 (LAT1) expression increases in well-differentiated but decreases in poorly differentiated endometrial endometrioid adenocarcinoma, and shows an inverse correlation with p53 expression.", Int J Gynecol Cancer. 24(4): 659-63, 2014.

Non Patent Literature 7: Sakata et al., "L-type amino-acid transporter 1 as a novel biomarker for high-grade malignancy in prostate cancer.", Pathol Int. 59(1):7-18, 2009.

Non Patent Literature 8: Kaira K et al., "L-type amino acid transporter 1 and CD98 expression in primary and metastatic sites of human neoplasms.", Cancer Sci. 99(12): 2380-6, 2008.

SUMMARY OF INVENTION

Technical Problem

PD-L1 and LAT1 reside in the cell membrane of cancer cells composing cancer tissues. These have each been suggested to be associated with the malignancy of cancer, but there has yet been no clear report on whether these two cancer-specific proteins have been related to each other.

An object of the present invention is to provide a new biomarker that can be used to predict the response to an anti-PD-1 antibody or an anti-PD-L1 antibody therapy. Another object of the present invention is to reveal the connection between PD-L1 and LAT1.

Many cancer cells composing a particular cancer (lung cancer, gastric cancer, colorectal cancer and the like) tissue are not homogeneous, but unequal. Because situations of patients having cancers with the same disease name are all different, personalized medicine is considered to be the principle of anticancer therapies. The present inventors have considered that cancer tissues of many heterogenic patients can be roughly classified into some subtypes by employing the two cancer markers PD-L1 and LAT1, and actually attempted the classification. As a result, cancer tissues was able to be classified into the 3 types: cancer tissues having high PD-L1 expression levels (P-predominant type), cancers having high LAT1 expression levels (L-predominant type), and cancers comprising cells expressing both PD-L1 and LAT1 and having high PD-L1 and LAT1 expression levels (PL-coexisting type), as summarized in Table 1.

TABLE 1

|  | LAT1 Expression | PD-L1 Expression | PDL-1 & LAT1 Expressions in the same cell | Figure |
| --- | --- | --- | --- | --- |
| P-predominant type | Low | High | Absent | FIG. 1 |
| L-predominant type | High | Absent to Low | Absent | FIG. 2 |
| PL- coexistent type | High | High | Present | FIG. 3 |

Solution to Problem

The present inventors have found that LAT1 serves as a new biomarker for cancer and thereby completed the present invention. More specifically, the present invention provides a method for predicting a response of a subject to an anti-PD-1 antibody or an anti-PD-L1 antibody therapy, comprising steps of: measuring an expression level of LAT1 in a sample collected from a cancer tissue of the subject; and predicting a response of the subject to the anti-PD-1 antibody or anti-PD-L1 antibody therapy based on the expression level of LAT1.

In the aforementioned method, the response to the anti-PD-1 antibody or anti-PD-L1 antibody therapy may be predicted based on a combination of the expression level of LAT1 and the expression level of PD-L1. More specifically, the aforementioned method may further comprise a step of measuring an expression level of PD-L1 in the sample collected from the cancer tissue of the subject, and the prediction in the step of predicting a response of the subject to the anti-PD-1 antibody or anti-PD-L1 antibody therapy may be performed based on the expression levels of LAT1 and PD-L1.

In the aforementioned method, the anti-PD-1 antibody may be nivolumab.

In the aforementioned method, the cancer may be lung cancer, may be non-small cell lung cancer, and may be lung adenocarcinoma.

In the aforementioned method, the measurement of the expression levels of LAT1 and PD-L1 may be performed using immunohistochemistry.

In the aforementioned method, the immunohistochemistry may be performed in various conditions. Examples of the various conditions of the immunohistochemistry are shown in Table 2. In the immunohistochemistry for staining LAT1 only, the staining may be single staining of a single section with anti-LAT1 antibody. In the immunohistochemistry for staining PD-L1 only, the staining may be single staining of a single section with anti-PD-L1 antibody. In the immunohistochemistry for staining both PD-L1 and LAT1, the staining may be performed by preparing 2 serial sections, performing single staining of one of the sections with an anti-PD-L1 antibody, and performing single staining of the other section with an anti-LAT1 antibody. Alternatively, in the immunohistochemistry for staining both PD-L1 and LAT1, the staining may be double staining of a single section with an anti-PD-L1 antibody and an anti-LAT1 antibody. In the single staining, PD-L1 and LAT1 may be stained in the same color, for example, brown (DAB dye). In the double staining, different cancer markers may be stained in different colors, for example, with green and red dyes. The accuracy of the determination varies depending on the conditions. Moreover, prior to the immunohistochemistry, the shape of cells may be observed by hematoxylin-eosin staining usually used in histopathology.

TABLE 2

| To be stained | Sample | Staining | Accuracy | Figure |
| --- | --- | --- | --- | --- |
| LAT1 | Single section | Single staining | Low | — |
| PD-L1 | Single section | Single staining | Low | FIG. 4 |
| PD-L1&LAT1 | Serial 2 sections | Single staining | Intermediate | FIG. 5 |
| PD-L1&LAT1 | Single section | Double staining | High | FIGS. 6 and 7 |

Namely, the immunohistochemistry may comprise performing single staining of a single section prepared from a sample collected from a cancer tissue of the subject, may comprise performing single staining of serial sections prepared from a sample collected from a cancer tissue of the subject, or may comprise performing double staining of a single section prepared from a sample collected from a cancer tissue of the subject.

Moreover, the present inventors have found that the PL-coexistent type of cancer patients have bad prognoses. Accordingly, the present invention also provides a method for evaluating a malignancy of cancer in a subject. Such a method comprises steps of: staining a sample collected from a cancer tissue of the subject with an anti-LAT1 antibody and an anti-PD-L1 antibody; and evaluating a malignancy of the cancer in the subject based on a presence or absence of a LAT1-positive and PD-L1-positive site. The cancer may be lung cancer, colorectal cancer, pancreatic cancer, or biliary cancer. The staining step may comprise performing single staining of serial sections prepared from a sample collected from a cancer tissue of the subject and may comprise performing double staining of a single section prepared from a sample collected from a cancer tissue of the subject.

Furthermore, the present invention also provides a method for treating cancer and a method for increasing response of an anti-PD-1 antibody or anti-PD-L1 antibody therapy, described below.

[1] A method for treating cancer, comprising steps of: measuring expression levels of LAT1 and PD-L1 in a sample collected from a cancer tissue of a subject; predicting a response of the subject to an anti-PD-1 antibody or anti-PD-L1 antibody therapy based on the expression levels of LAT1 and PD-L1; and administering an anti-PD-1 antibody or an anti-PD-L1 antibody to the subject predicted to be likely to receive a therapeutic benefit from the anti-PD-1 antibody or anti-PD-L1 antibody therapy.

[2] The method according to [1], wherein the anti-PD-1 antibody or anti-PD-L1 antibody and a LAT1 inhibitor are administered in the step of administering an anti-PD-1 antibody or an anti-PD-L1 antibody to the subject predicted to be likely to receive a therapeutic benefit from the anti-PD-1 antibody or anti-PD-L1 antibody therapy.

[3] A method for treating cancer, comprising steps of: measuring an expression level of LAT1 in a sample collected from a cancer tissue of a subject; predicting a response of the subject to an anti-PD-1 antibody or anti-PD-L1 antibody therapy based on the expression level of LAT1; and administering an anti-PD-1 antibody or an anti-PD-L1 antibody and a LAT1 inhibitor to the subject predicted to be unlikely to receive a therapeutic benefit from the anti-PD-1 antibody or anti-PD-L1 antibody therapy.

[4] The method according to any one of [1] to [3], wherein the anti-PD-1 antibody is nivolumab.

[5] The method according to any one of [1] to [4], wherein the cancer is lung cancer.

[6] The method according to [5], wherein the lung cancer is non-small cell lung cancer.

[7] The method according to [6], wherein the non-small cell lung cancer is lung adenocarcinoma.

[8] The method according to any one of [1] to [7], wherein the measurement of the expression level is performed by immunohistochemistry.

[9] The method according to any one of [1] to [7], wherein the measurement of the expression level of LAT1 is performed by immunohistochemistry, and the immunohistochemistry comprises single staining of a single section prepared from the sample.

[10] The method according to [1], wherein the measurement of the expression level of LAT1 and the measurement of the expression level of PD-L1 are performed by immunohistochemistry, and the immunohistochemistry comprises single staining of serial sections prepared from the sample.

[11] The method according to [1], wherein the measurement of the expression level of LAT1 and the measurement of the expression level of PD-L1 are performed by immunohistochemistry, and the immunohistochemistry comprises double staining of a single section prepared from the sample.

[12] A method for increasing response to an anti-PD-1 antibody or anti-PD-L1 antibody therapy, comprising: administering an anti-PD-1 antibody or an anti-PD-L1 antibody and a LAT1 inhibitor to a subject.

[13] The method according to [12], wherein the subject is a subject predicted to be likely to receive a therapeutic benefit from the anti-PD-1 antibody or anti-PD-L1 antibody therapy based on the expression levels of LAT1 and PD-L1 in a sample collected from a cancer tissue of the subject.

[14] The method according to [12], wherein the subject is a subject predicted to be unlikely to receive a therapeutic benefit from the anti-PD-1 antibody or anti-PD-L1 antibody therapy based on the expression level of LAT1 in a sample collected from a cancer tissue of the subject.

Furthermore, the present invention also provides an anticancer compound and use thereof, an anticancer agent, a kit, and a pharmaceutical composition, described below.

[15] O-(5-Amino-2-phenylbenzoxazol-7-yl)methyl-3,5-dichloro-L-tyrosine or a pharmacologically acceptable salt thereof, characterized in that O-(5-Amino-2-phenylbenzoxazol-7-yl)methyl-3,5-dichloro-L-tyrosine or the pharmacologically acceptable salt thereof is administered in combination with an anti-PD-1 antibody or an anti-PD-L1 antibody, wherein O-(5-amino-2-phenylbenzoxazol-7-yl)methyl-3,5-dichloro-L-tyrosine or the pharmacologically acceptable salt thereof is administered simultaneously with or separately from the anti-PD-1 antibody or anti-PD-L1 antibody.

[16] An anticancer agent comprising a combination of an anti-PD-1 antibody or an anti-PD-L1 antibody and O-(5-amino-2-phenylbenzoxazol-7-yl)methyl-3,5-dichloro-L-tyrosine or a pharmacologically acceptable salt thereof.

[17] A kit for treating cancer, comprising a combination of an anti-PD-1 antibody or an anti-PD-L1 antibody and O-(5-amino-2-phenylbenzoxazol-7-yl)methyl-3,5-dichloro-L-tyrosine or a pharmacologically acceptable salt thereof.

[18] A pharmaceutical composition for treating cancer, comprising an anti-PD-1 antibody or an anti-PD-L1 antibody and O-(5-amino-2-phenylbenzoxazol-7-yl)methyl-3,5-dichloro-L-tyrosine or a pharmacologically acceptable salt thereof.

[19] O-(5-Amino-2-phenylbenzoxazol-7-yl)methyl-3,5-dichloro-L-tyrosine or a pharmacologically acceptable salt thereof, for use in the treatment of cancer, characterized in that O-(5-Amino-2-phenylbenzoxazol-7-yl)methyl-3,5-dichloro-L-tyrosine or the pharmacologically acceptable salt thereof is administered in combination with an anti-PD-1 antibody or an anti-PD-L1 antibody, wherein O-(5-amino-2-phenylbenzoxazol-7-yl)methyl-3,5-dichloro-L-tyrosine or the pharmacologically acceptable salt thereof is administered simultaneously with or separately from the anti-PD-1 antibody or anti-PD-L1 antibody.

[20] Use of O-(5-amino-2-phenylbenzoxazol-7-yl)methyl-3,5-dichloro-L-tyrosine or a pharmacologically acceptable salt thereof for the manufacture of a medicament, characterized in that O-(5-amino-2-phenylbenzoxazol-7-yl)methyl-3,5-dichloro-L-tyrosine or the pharmacologically acceptable salt thereof is administered in combination with an anti-PD-1 antibody or an anti-PD-L1 antibody, wherein O-(5-amino-2-phenylbenzoxazol-7-yl)methyl-3,5-dichloro-L-tyrosine or the pharmacologically acceptable salt thereof is administered simultaneously with or separately from the anti-PD-1 antibody or anti-PD-L1 antibody.

Advantageous Effects of Invention

According to the present invention, it is possible to predict the response to an anti-PD-1 antibody or anti-PD-L1 antibody therapy, to evaluate a malignancy of cancer, or to increase the response to an anti-PD-1 antibody or anti-PD-L1 antibody therapy.

DESCRIPTION OF EMBODIMENTS

Figure 1:
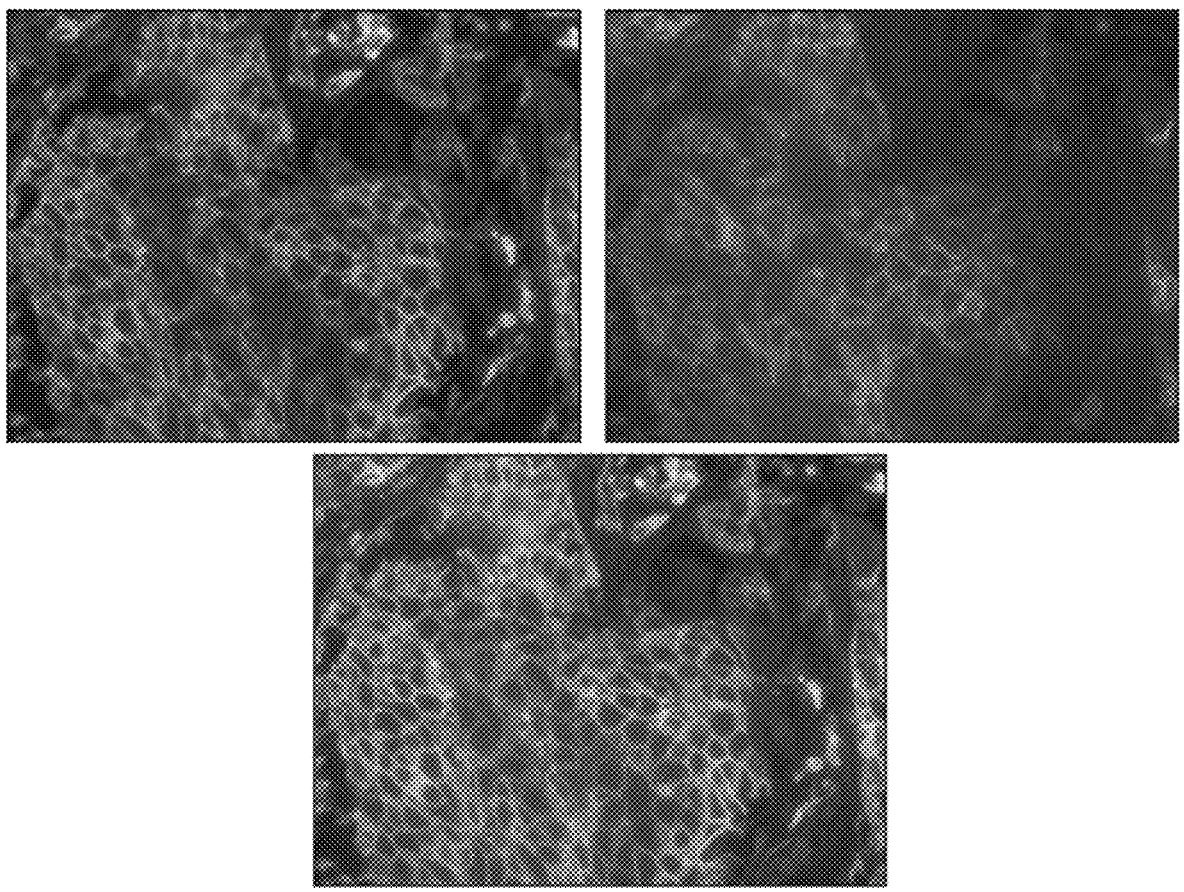
FIG. 1 shows an example of a cancer having high PD-L1 expression level, which was classified into the P-predominant type by the cancer tissue typing shown in Table 1.

An anti-PD-1 antibody therapy and an anti-PD-L1 antibody therapy are methods for treating cancer that involve administering an anti-PD-1 antibody and an anti-PD-L1 antibody, respectively, to patients. Examples of the anti-PD-1 antibody include human anti-human PD-1 monoclonal antibodies such as nivolumab and pembrolizumab. Examples of the anti-PD-L1 antibody include human anti-human PD-L1 monoclonal antibodies such as atezolizumab, avelumab, and durvalumab.

It is important from the viewpoint of medical economy and the viewpoint of QOL (quality of life) of patients to predict, before administering an anti-PD-1 antibody or an anti-PD-L1 antibody, whether patients respond to the anti-PD-1 antibody or anti-PD-L1 antibody. A method for predicting a response to an anti-PD-1 antibody or anti-PD-L1 antibody therapy according to one embodiment of the present invention involves measuring an expression level of LAT1 in a sample collected from a cancer tissue of a subject and predicting a response of the subject to the anti-PD-1 antibody or anti-PD-L1 antibody therapy based on the expression level of LAT1. A method for predicting a response to an anti-PD-1 antibody or anti-PD-L1 antibody therapy according to another embodiment of the present invention involves measuring expression levels of LAT1 and PD-L1 in a sample collected from a cancer tissue of a subject and predicting a response of the subject to the anti-PD-1 antibody or anti-PD-L1 antibody therapy based on the expression levels of LAT1 and PD-L1. Using both LAT1 and PD-L1 as biomarkers makes it possible to predict the response more accurately than using LAT1 alone or PD-L1 alone as a biomarker.

The method for measuring expression levels of LAT1 and PD-L1 in a sample collected from a cancer tissue of a subject is not particularly limited, and examples thereof include known methods such as immunohistochemistry and ELISA (enzyme-linked immunosorbent assay).

The response of the subject to the anti-PD-1 antibody or anti-PD-L1 antibody therapy is predicted based on the expression level of LAT1. The criteria of the prediction of the response may be established as follows: (a) subjects having a low LAT1 expression are likely to receive a therapeutic benefit therefrom; and (b) subjects having a high LAT1 expression are unlikely to receive a therapeutic benefit therefrom. Whether the expression of LAT1 is high or low depends on the method of measurement, and in immunohistochemistry, for example, cases where LAT1-positive cells are less than 25% of the total cells in the sample may be defined as low LAT1 expression, and cases where LAT1-positive cells are 25% or more may be defined as high LAT1 expression.

It is also possible to predict the response of the subject to the anti-PD-1 antibody or anti-PD-L1 antibody therapy based on the expression levels of LAT1 and PD-L1. The criteria of the prediction of the response may be established as follows: (c) subjects having a low LAT1 expression and a high PD-L1 expression are likely to receive a therapeutic benefit therefrom; and (d) subjects having a high LAT1 expression and a low PD-L1 expression are unlikely to receive a therapeutic benefit therefrom. Whether the expression of PD-L1 is high or low depends on the method of measurement, and in immunohistochemistry, for example, cases where PD-L1-positive cells are less than 10% of the total cells in the sample may be defined as low PD-L1 expression, and cases where PD-L1-positive cells are 10% or more may be defined as high PD-L1 expression.

The cancer to be predicted about the response to the anti-PD-1 antibody or anti-PD-L1 antibody therapy is not particularly limited, and examples thereof include lung cancer, in particular, non-small cell lung cancer and lung adenocarcinoma.

In one embodiment, the present invention also provides a method for treating cancer. According to the method, an anti-PD-1 antibody or anti-PD-L1 antibody therapy may be performed based on a result obtained by the aforementioned method for predicting a response to the anti-PD-1 antibody or anti-PD-L1 antibody therapy. Specifically, the method for treating cancer according to one embodiment of the present invention comprises steps of: measuring expression levels of LAT1 and PD-L1 in a sample collected from a cancer tissue of a subject; predicting a response of the subject to an anti-PD-1 antibody or anti-PD-L1 antibody therapy based on the expression levels of LAT1 and PD-L1; and administering an anti-PD-1 antibody or an anti-PD-L1 antibody to a subject predicted to be likely to receive a therapeutic benefit from the anti-PD-1 antibody or anti-PD-L1 antibody therapy. The details of the method for predicting a response to an anti-PD-1 antibody or anti-PD-L1 antibody therapy are as described above. The method of the administration of the anti-PD-1 antibody or anti-PD-L1 antibody to the subject is not particularly limited, and the anti-PD-1 antibody or anti-PD-L1 antibody may be administered, for example, by intravenous injection.

In combination with the anti-PD-1 antibody or anti-PD-L1 antibody, a LAT1 inhibitor may be administered to the aforementioned patient. The anti-PD-1 antibody or anti-PD-L1 antibody and the LAT1 inhibitor may be administered simultaneously or separately. The LAT1 inhibitor is not particularly limited and may be, for example, O-(5-amino-2-phenylbenzoxazol-7-yl)methyl-3,5-dichloro-L-tyrosine. The method of the administration of the LAT1 inhibitor is not particularly limited, and the LAT1 inhibitor may be administered, for example, by intravenous injection. According to the new discovery by the present inventors, PD-L1 and LAT1 are mutually related and, to be surprised, decrease of LAT1 in expression or activity increases expression of PD-L1. Accordingly, the PD-L1 expression level in cancer cells in a patient may be increased by decreasing the expression level or activity of LAT1 in the cancer cells in the patient by a LAT1 inhibitor. Since it is considered that the higher expression levels of PD-L1 result in the higher therapeutic benefits from an anti-PD-1 antibody or an anti-PD-L1 antibody, the administration of an anti-PD-1 antibody or an anti-PD-L1 antibody in combination with a LAT1 inhibitor can provide a more prominent anticancer effect in comparison with the administration of the anti-PD-1 antibody or anti-PD-L1 antibody alone.

Moreover, the method for treating cancer according to another embodiment of the present invention comprises steps of: measuring an expression level of LAT1 in a sample collected from a cancer tissue of the subject; predicting a response of the subject to an anti-PD-1 antibody or anti-PD-L1 antibody therapy based on the expression level of LAT1; and administering an anti-PD-1 antibody or an anti-PD-L1 antibody and a LAT1 inhibitor to a subject predicted to be unlikely to receive a therapeutic benefit from the anti-PD-1 antibody or anti-PD-L1 antibody therapy. The anti-PD-1 antibody or anti-PD-L1 antibody and the LAT1 inhibitor may be administered simultaneously or separately. Patients having high LAT1 expression levels (patients of the L-predominant type or the PL-coexistent type) may be predicted to exhibit low response to the administration of an anti-PD-1 antibody or an anti-PD-L1 antibody alone. However, since the LAT1 inhibitor can not only reduce the expression level or activity of LAT1 in patients, but also increase the PD-L1 expression level, as described above, combined use of the anti-PD-1 antibody or anti-PD-L1 antibody and the LAT1 inhibitor can provide to patients of the L-predominant type or the PL-coexistent type, having intrinsically high LAT1 expression level, an anticancer effect at a level equivalent to the anticancer effect provided to the P-predominance type, having low LAT1 expression level and high PD-L1 expression level.

From the same viewpoint, it can be said that one embodiment of the present invention is to provide a method for increasing response to an anti-PD-1 antibody or anti-PD-L1 antibody therapy, comprising combined use of an anti-PD-1 antibody or anti-PD-L1 antibody therapy and a LAT1 inhibition therapy. Such a method comprises administering an anti-PD-1 antibody or an anti-PD-L1 antibody and a LAT1 inhibitor to a subject. The subject may be a subject predicted to be likely to receive a therapeutic benefit from the anti-PD-1 antibody or anti-PD-L1 antibody therapy based on the expression levels of LAT1 and PD-L1 in a sample collected from a cancer tissue of the subject or a subject predicted to be unlikely to receive a therapeutic benefit from the anti-PD-1 antibody or anti-PD-L1 antibody therapy based on the expression level of LAT1 in a sample collected from a cancer tissue of the subject.

Figure 16:
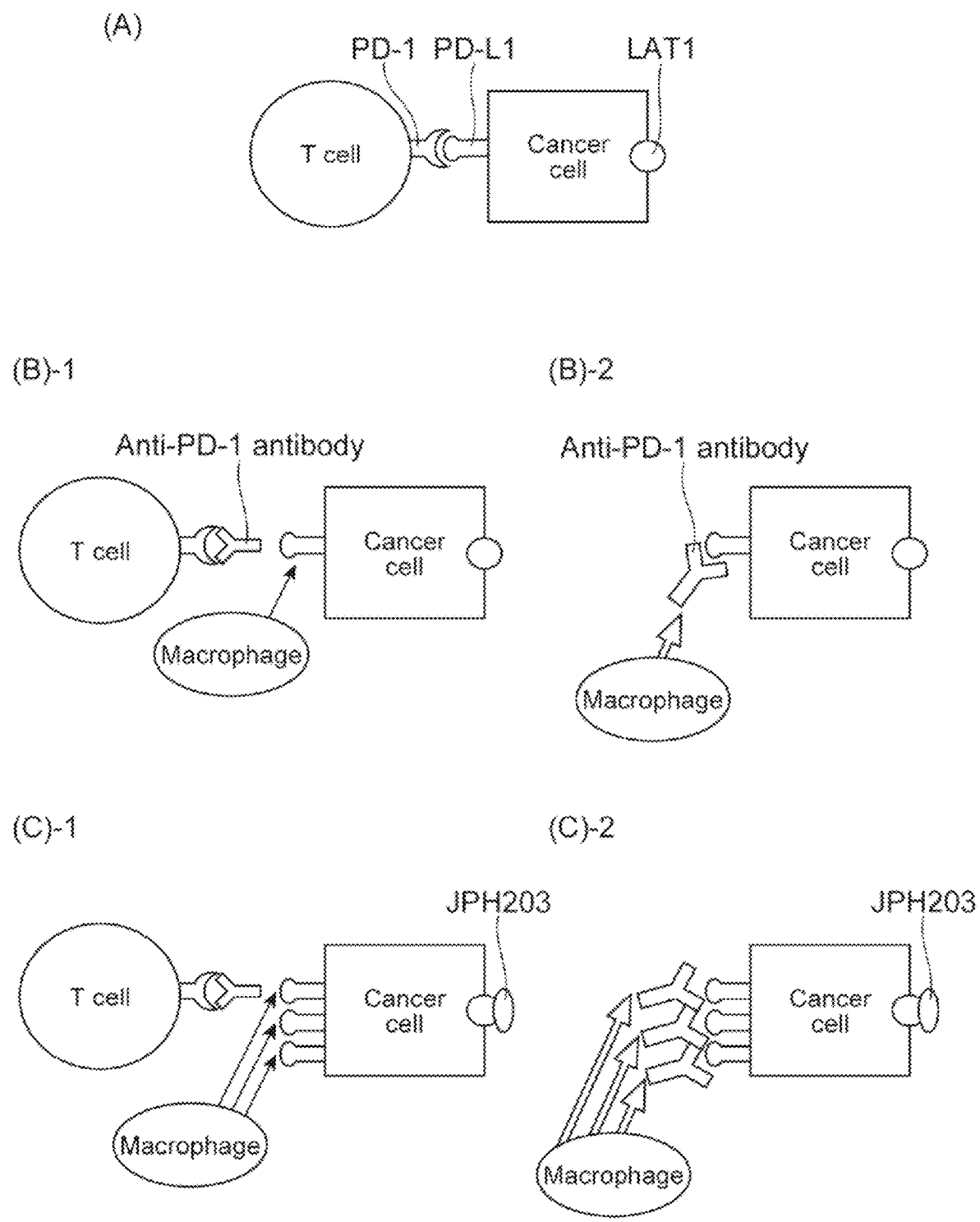
FIG. 16 is a schematic diagram illustrating the mechanisms of action of an anti-PD-1 antibody, an anti-PD-L1 antibody, and a LAT1 inhibitor.

The mechanisms of action of an anti-PD-1 antibody, an anti-PD-L1 antibody, and a LAT1 inhibitor are shown in FIG. 16. FIG. 16 (A) illustrates a T cell and a cancer cell in a patient undergoing no anticancer therapy. In the absence of an anti-PD-1 antibody or anti-PD-L1 antibody, PD-1 on the T cell and PD-L1 on the cancer cell can bind to each other.

As illustrated in FIG. 16 (B)-1, the administration of an anti-PD-1 antibody to the patient inhibits binding between PD-1 and PD-L1. Since this makes it possible for macrophages to recognize PD-L1, the anticancer effect is exerted. Meanwhile, the administration of the anti-PD-L1 antibody to the patient allows the anti-PD-L1 antibody and PD-L1 on the cancer cell to bind to each other, as illustrated in FIG. 16 (B)-2. Since this makes it possible for macrophages to recognize PD-L1 strongly, the anticancer effect is exerted. The administration of a LAT1 inhibitor in addition to an anti-PD-1 antibody or an anti-PD-L1 antibody to a patient allows the LAT1 inhibitor to inhibit the activity of LAT1, as illustrated in FIGS. 16 (C)-1 and (C)-2, and therefore decreases the amino acid supply into cancer cells and increases the apoptosis of cancer cells. In addition to this, the LAT1 inhibitor increases the expression level of PD-L1 and allows more macrophages to recognize PD-L1, thereby increasing the response to the anti-PD-1 antibody or anti-PD-L1 antibody. Accordingly, the provision of more prominent anticancer effect is speculated to be possible.

A method for evaluating a malignancy of cancer in a subject, according to one embodiment of the present invention comprises steps of: staining a sample collected from a cancer tissue of the subject with an anti-LAT1 antibody and an anti-PD-L1 antibody; and evaluating a malignancy of the cancer in the subject based on a presence or absence of a LAT1-positive and PD-L1-positive site. The staining with the anti-LAT1 antibody and the anti-PD-L1 antibody may be performed by immunohistochemistry.

The present inventors have found that cancer tissues having high malignancy tend to comprise LAT1-positive and PD-L1-positive sites and cancer tissues having low malignancy tend to comprise no LAT1-positive and PD-L1-positive sites. Accordingly, the malignancy of cancer can be evaluated based on the presence or absence of LAT1-positive and PD-L1-positive sites.

The therapeutic strategy for a subject may be determined based on the evaluation of malignancy.

The cancer whose malignancy is to be evaluated is not particularly limited, and examples thereof include lung cancer, colorectal cancer, pancreatic cancer, and biliary cancer.

EXAMPLES

Staining Example 1

Cancer tissues were collected from 3 cancer patients and double staining of single sections with an anti-LAT1 antibody and an anti-PD-L1 antibody was performed. The results are shown in FIGS. 1 to 3.

FIG. 1 is an example of the result of staining of lung cancer tissue (magnification 400×). The upper left panel is a photograph when LAT1 was stained with a green dye, the upper right panel is a photograph when PD-L1 was stained with a red dye, and the lower panel is an overlay photograph of both. In this lung cancer tissue, PD-L1 is predominantly stained.

Figure 2:
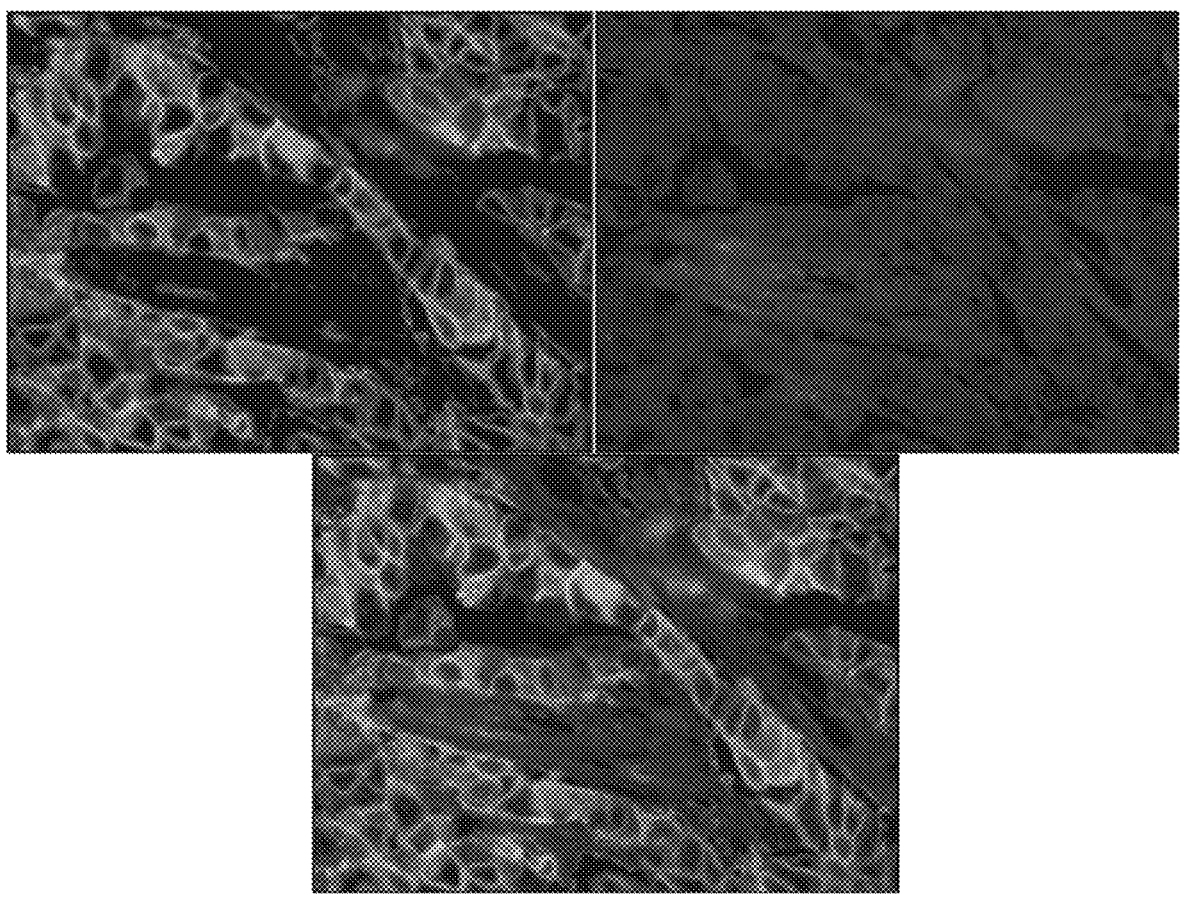
FIG. 2 shows an example of a cancer having high LAT1 expression level, which was classified into the L-predominant type by the cancer tissue typing shown in Table 1.

FIG. 2 is an example of the result of staining of breast cancer tissue (magnification 400×). The upper left panel is a photograph when LAT1 was stained with a green dye, the upper right panel is a photograph when PD-L1 was stained with a red dye, and the lower panel is an overlay photograph of both. In this breast cancer tissue, LAT1 is predominantly stained.

Figure 3:
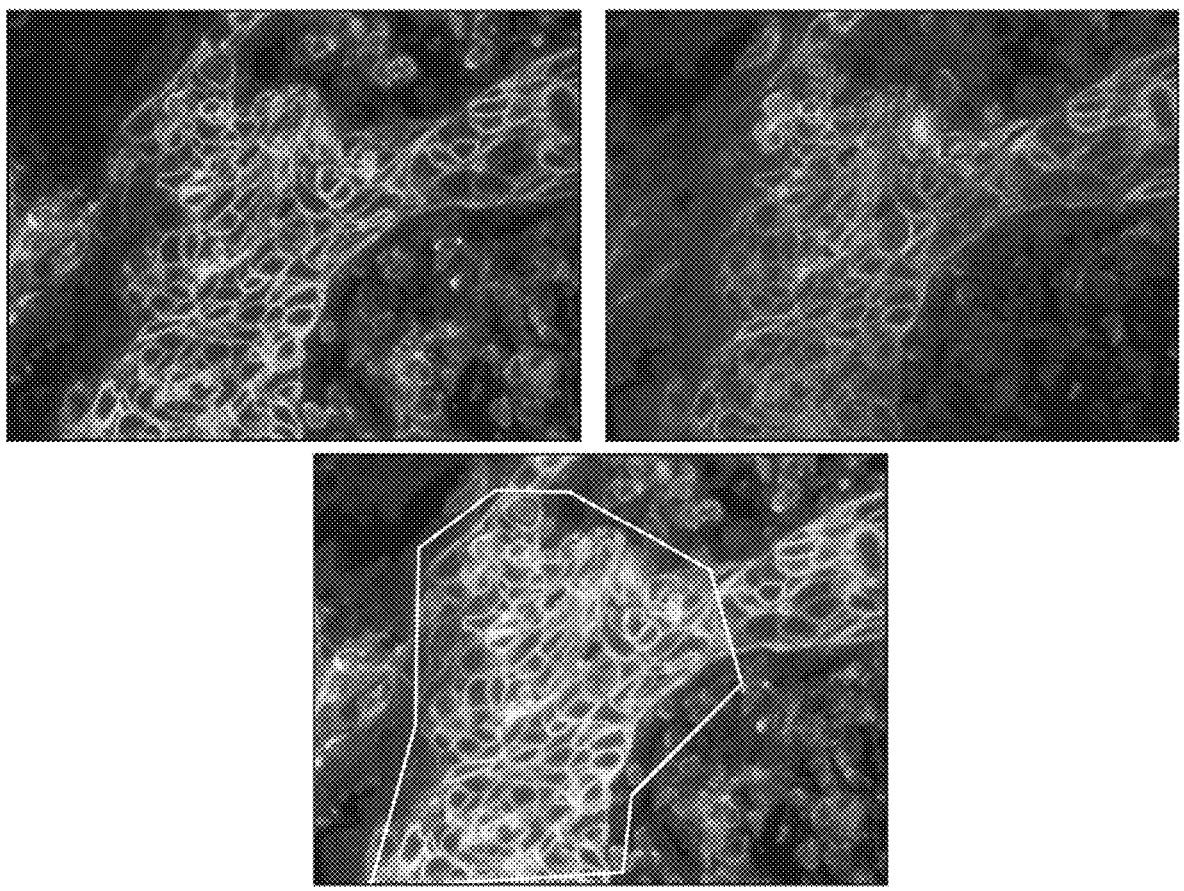
FIG. 3 shows an example of a cancer comprising cells expressing both PD-L1 and LAT1 and having high PD-L1 and LAT1 expression levels, which was classified into the PL-coexisting type by the cancer tissue typing shown in Table 1.

FIG. 3 is another example of the result of staining of lung cancer tissue (magnification 400×). The upper left panel is a photograph when LAT1 was stained with a green dye, the upper right panel is a photograph when PD-L1 was stained with a red dye, and the lower panel is an overlay photograph of both. A yellow staining image was seen in the part surrounded with the frame in the lower panel. The yellow staining image is the result of overlaying a red staining image and a green staining image and means that both PD-L1 and LAT1 are present in the part stained in yellow. Accordingly, this lung cancer tissue is an example of a cancer tissue of the PL-coexistent type, comprising cells expressing both PD-L1 and LAT1.

Staining Example 2

Figure 4:
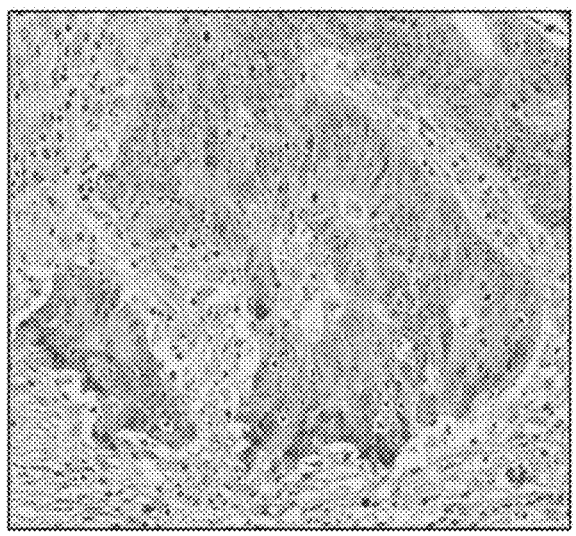
FIG. 4 shows an example of the result of staining a colorectal cancer tissue.
Figure 4:
Figure 4:
Figure 4:

A cancer tissue was collected from a colorectal cancer patient, and a single section was stained using hematoxylin-eosin (HE) and antibodies (anti-LAT1, anti-PD-1, and anti-PD-L1). The results are shown in FIG. 4 (magnification 200×). HE stains sections in purple and the antibodies stain sections in brown. The upper left panel is an HE staining image. The upper right panel is a staining image with the anti-LAT1 antibody. The lower left panel is a staining image with the anti-PD-1 antibody. The lower right panel is a staining image with the anti-PD-L1 antibody. In this colorectal cancer tissue, LAT1 was strongly positive.

Staining Example 3

Figure 5:
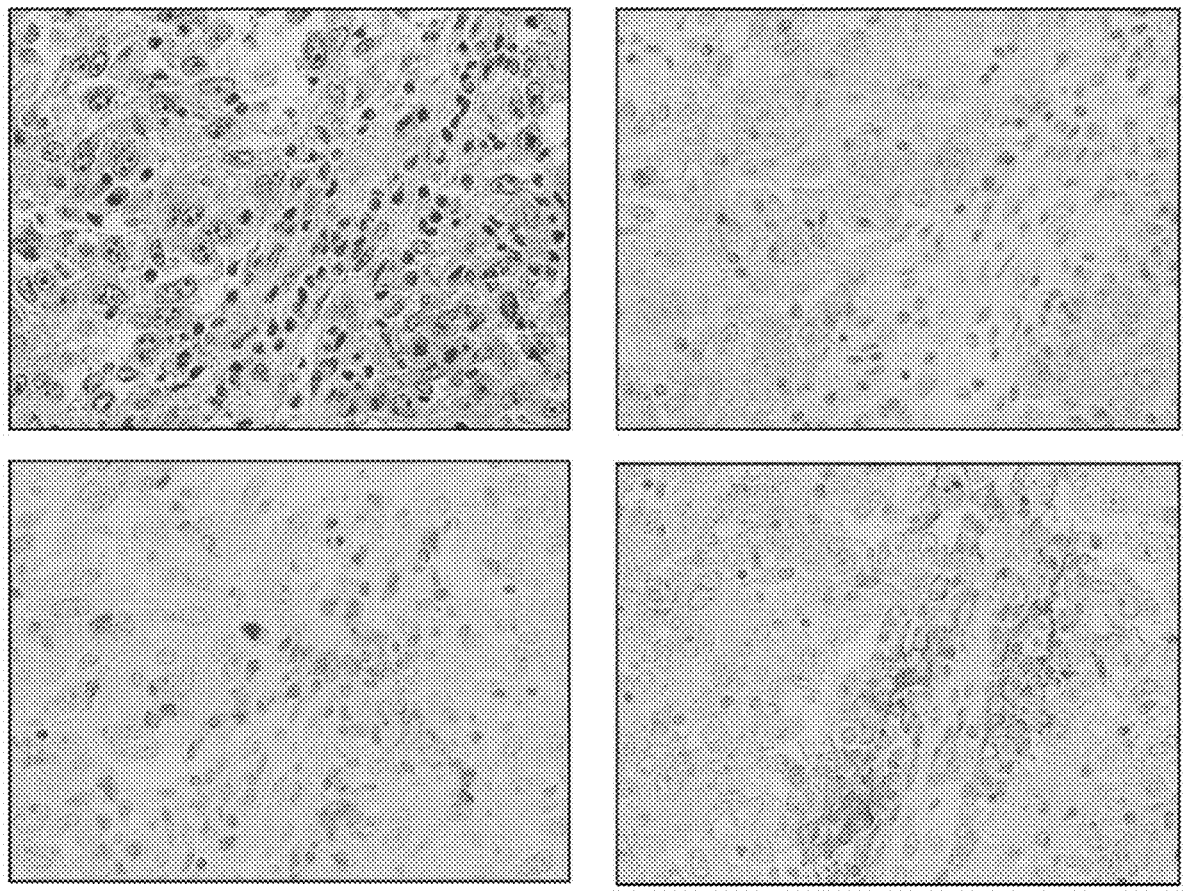
FIG. 5 shows an example of the result of staining serial sections of triple negative breast cancer.

A cancer tissue was collected from a triple negative breast cancer patient and serial sections were stained using HE and antibodies (anti-LAT1, anti-PD-1, and anti-PD-L1). The results are shown in FIG. 5 (magnification 400×). The upper left panel is an HE staining image. The upper right panel is a staining image with the anti-LAT1 antibody. The lower left panel is a staining image with the anti-PD-1 antibody. The lower right panel is a staining image with the anti-PD-L1 antibody. In this breast cancer tissue, PD-L1 was positive.

Staining Example 4

Figure 6:
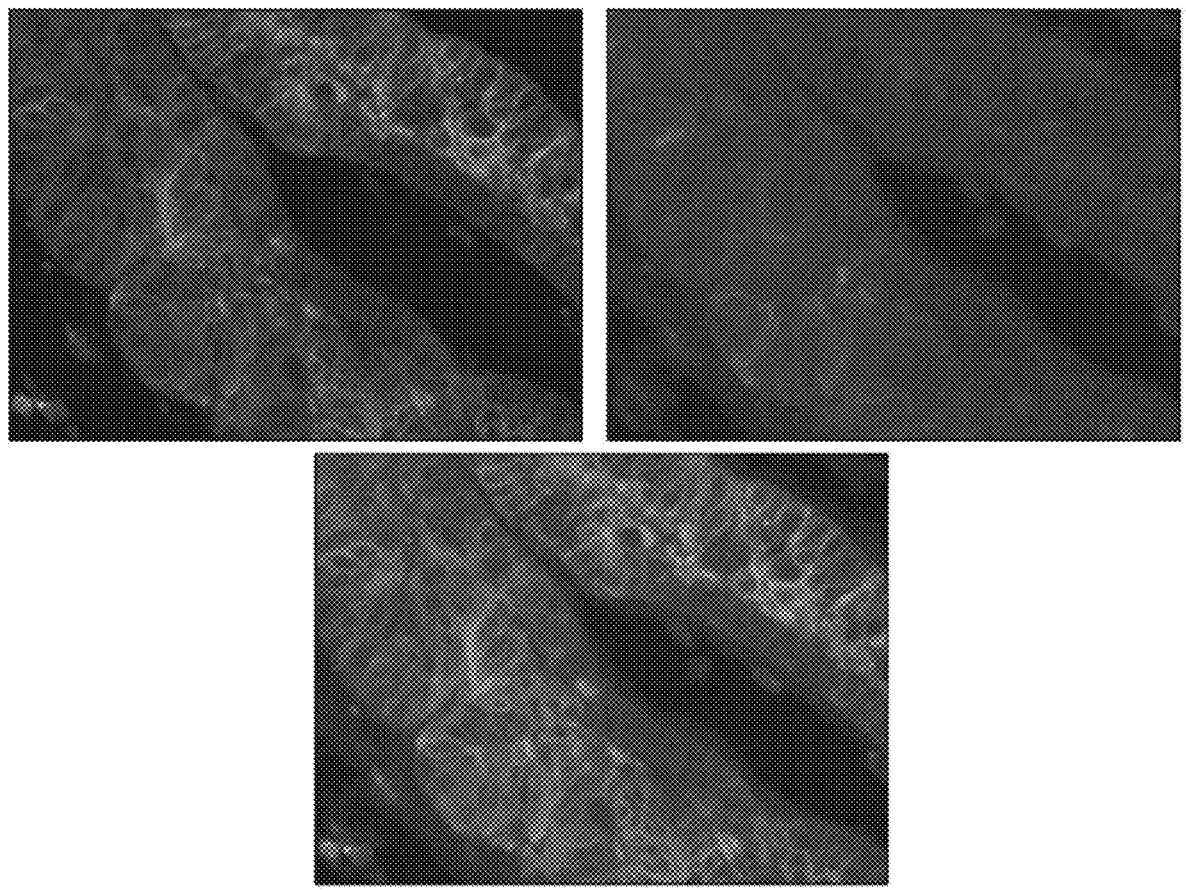
FIG. 6 shows an example of the result of staining a pancreatic cancer tissue.

A cancer tissue was collected from a pancreatic cancer patient and double staining of a single section with an anti-LAT1 antibody and an anti-PD-L1 antibody was performed. The results are shown in FIG. 6 (magnification 400×). The upper left panel is a photograph when LAT1 was stained with a green dye, the upper right panel is a photograph when PD-L1 was stained with a red dye, and the lower panel is an overlay photograph of both. The yellow color indicating the cancer tissue of the PL-coexistence type was not seen in the photograph of the lower panel.

Figure 7:
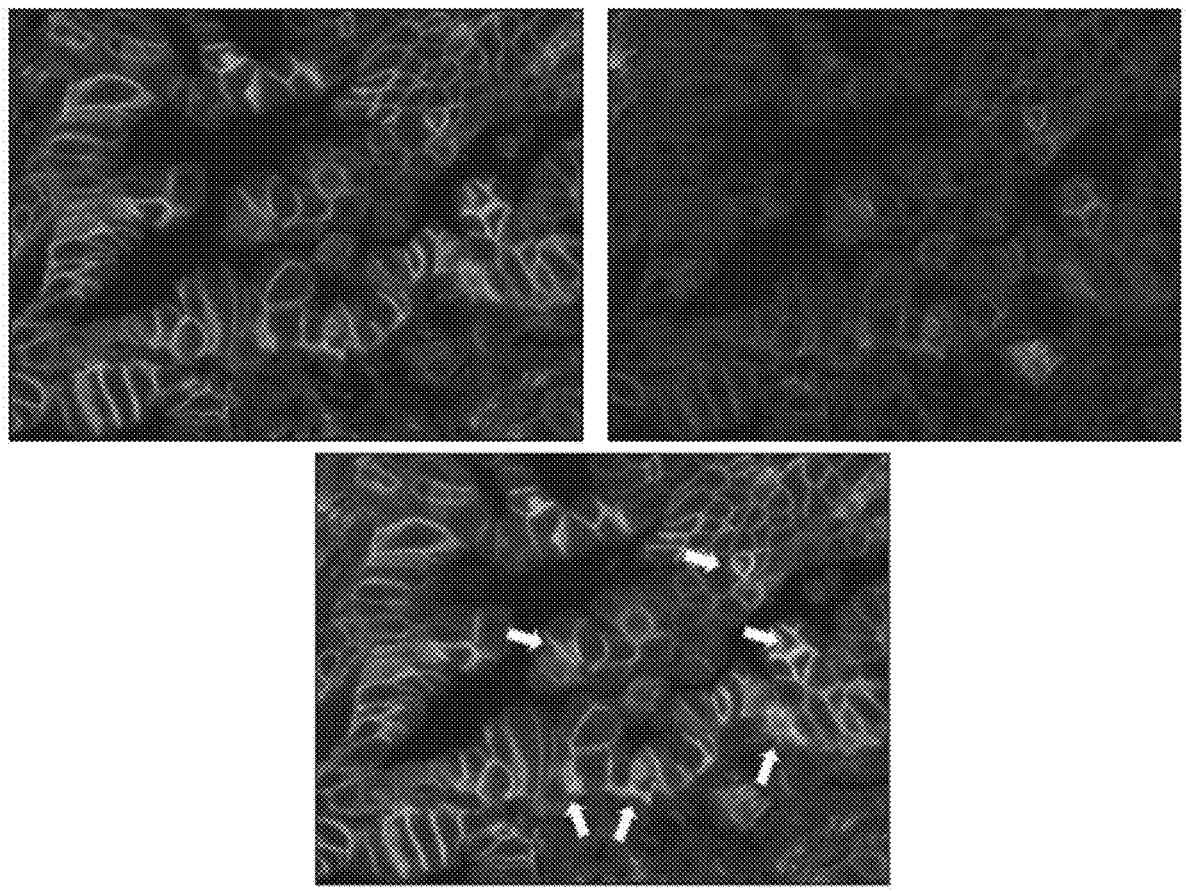
FIG. 7 shows another example of the result of staining a pancreatic cancer tissue.

The results for a cancer tissue from another pancreatic cancer patient are shown in FIG. 7. The upper left panel is a photograph when LAT1 was stained with a green dye, the upper right panel is a photograph when PD-L1 was stained with a red dye, and the lower panel is an overlay photograph of both. Yellow positive observations (the parts indicated with the arrows) indicating the cancer tissue of the PL-coexistent type were clearly found in the photograph of the lower panel.

(Test Example 1) Prediction of Response to Nivolumab in Non-Small Cell Lung Cancer (1)

In the following Test Examples 1 to 3, the prediction of response to nivolumab based on the expression level of LAT1 or a combination of the expression level of LAT1 and the expression level of PD-L1 was examined. Cancer tissues were collected from 21 patients with first line anticancer therapy resistant/relapsed advanced non-small cell lung cancers (Stage III/IV) incorporated in this examination, and the expressions of LAT1 and PD-L1 were examined by immunohistochemistry using an anti-LAT1 antibody and an anti-PD-L1 antibody. Criteria of high expression and low expression for PD-L1 and LAT1 expression are shown in Table 3 and Table 4. Tumors were determined as positive when the cell membrane of the tumors, together with PD-L1 and LAT1, were stained. Tumors having 10% or more of PD-L1-positive cells were defined as having high PD-L1 expression, and tumors having 25% or more of LAT1-positive cells were defined as having high LAT1 expression.

TABLE 3

| PD-L1 | Score | Percentage of PD-L1 expressing cells |
|---|---|---|
| Low expression | 1 | <1% |
|  | 2 | 1-5% |
|  | 3 | 5-10% |
| High expression | 4 | 10-25% |
|  | 5 | 25-50% |
|  | 6 | >50% |

TABLE 4

| LAT1 | Score | Percentage of LAT1 expressing cells |
|---|---|---|
| Low expression | 1 | <10% |
|  | 2 | 10-25% |
| High expression | 3 | 25-50% |
|  | 4 | >50% |

Backgrounds of 21 patients (Stage III/IV) with non-small cell lung cancers are shown in Table 5.

TABLE 5

|  |  | Total patients (n = 21) | LAT1 expression High expression (n = 9) | LAT1 expression Low expression (n = 12) | p value |
|---|---|---|---|---|---|
| Age | less than/equal to or higher than 65 years old | 9/12 | 5/4 | 4/8 | 0.396 |
| Sex | Male/Female | 16/5 | 6/3 | 10/2 | 0.611 |
| PS, ECOG | 0/1 or 2 | 5/16 | 4/5 | 1/11 | 0.119 |
| Tissue type | Adenocarcinoma/Squamous cell carcinoma | 17/4 | 8/1 | 9/3 | 0.603 |
| PD-L1 expression | High expression/Low expression | 8/13 | 1/8 | 7/5 | 0.066 |

PS, ECOG represents Performance Status by Eastern Cooperative Oncology Group.

p values represent differences of clinicopathologic factors between high and low LAT1 expressions.

Subsequently, nivolumab was administered to the patients and the response to nivolumab was examined. The therapeutic benefit from nivolumab was determined by CT (computed tomography) in accordance with RECIST (Response Evaluation Criteria in Solid Tumors). The response rate was evaluated in accordance with the international criteria for which the tumor sizes are measured by CT and the tumors are classified into response, progression, or stable. The response refers to cases where 30% or more decrease is observed in the longer axis of the tumor after the administration of the agent. The progression refers to cases where the 20% or more increase is observed in the longer axis of the tumor after the administration of the agent. The stable refers to cases where the shrinkage of the tumor is insufficient to classify it as response and the increase of the tumor in comparison with the minimum sum of the longest axis after the start of the therapy is insufficient to classify it as progression.

Figure 8:
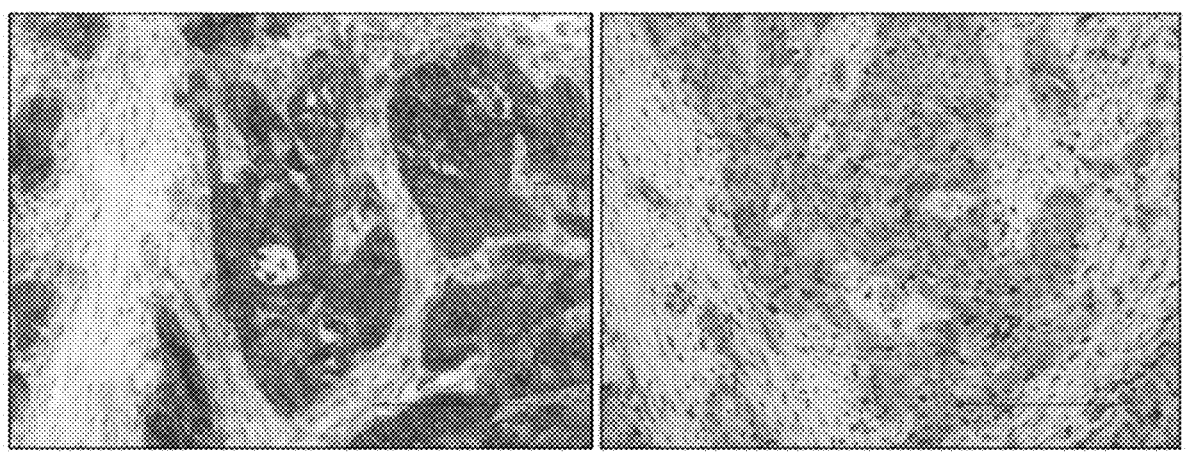
FIG. 8 shows an example of immunohistological pathological images of PD-L1 and LAT1 expressions in a lung cancer patient given nivolumab.
Figure 9:
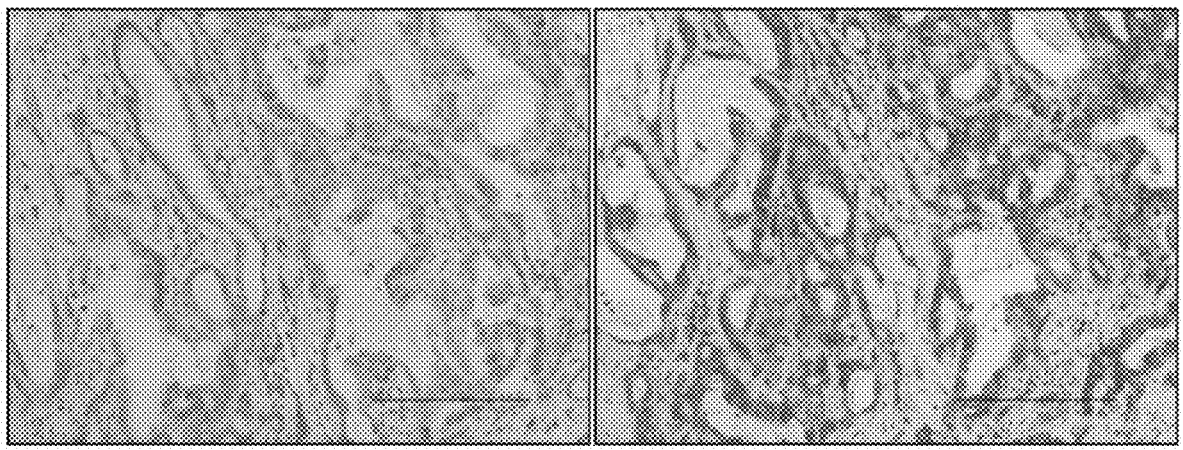
FIG. 9 shows another example of immunohistological pathological images of PD-L1 and LAT1 expression in a lung cancer patient given nivolumab.
Figure 10:
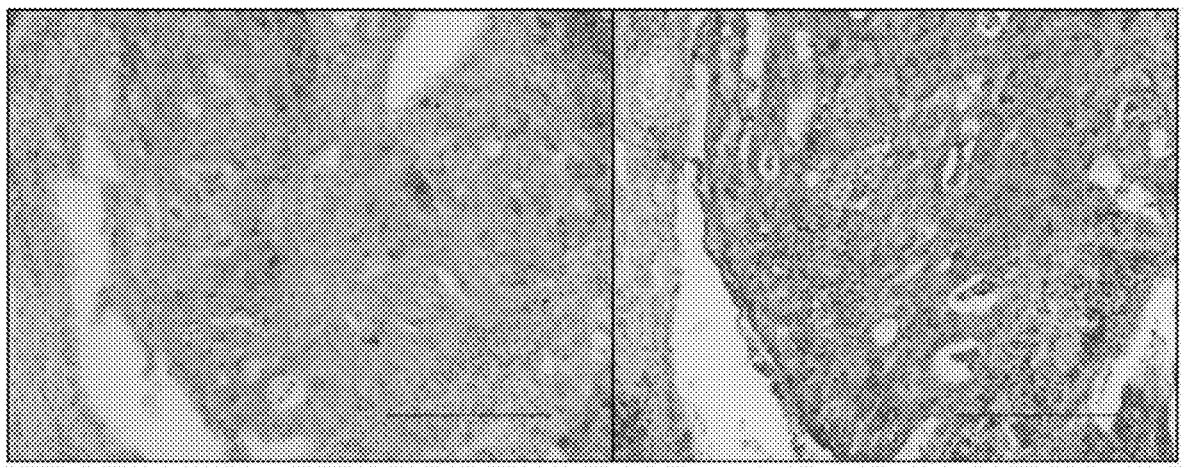
FIG. 10 shows further example of immunohistological pathological images of PD-L1 and LAT1 expressions in a lung cancer patient given nivolumab.

Immunohistological pathological images of LAT1 and PD-L1 expression in some patients are shown in FIGS. 8 to 10.

FIG. 8 shows the results of staining of a cancer tissue before the treatment of the patient that responded to a nivolumab treatment and achieved 10 or more months of progression-free survival (magnification 200×). The left panel shows a staining image with a PD-L1 antibody, and the right panel shows a staining image with a LAT1 antibody. While PD-L1 showed high expression, LAT1 showed low expression.

FIG. 9 shows the results of staining of a cancer tissue before the treatment of the patient that had progression in a nivolumab treatment (magnification 200×). The left panel shows a staining image with a PD-L1 antibody, and the right panel shows a staining image with a LAT1 antibody. While LAT1 showed high expression, PD-L1 showed low expression.

FIG. 10 shows the results of staining of a cancer tissue before the treatment of the patient that had progression in a nivolumab treatment (magnification 200×). The left panel shows a staining image with a PD-L1 antibody and the right panel shows a staining image with a LAT1 antibody. Both the expression of PD-L1 and the expression of LAT1 were high expression.

From the results of FIGS. 8 to 10, it was suggested that patients having a high PD-L1 expression and a low LAT1 expression (patients of the P-predominant type) exhibit high responses to the nivolumab treatment and patients having low PD-L1 expression and high LAT1 expression (patients of the L-predominant type) and patients having high expression of both PD-L1 and LAT1 (patients of the PL-coexistent type) exhibit no responses or low responses to a treatment using nivolumab alone.

Figure 11:
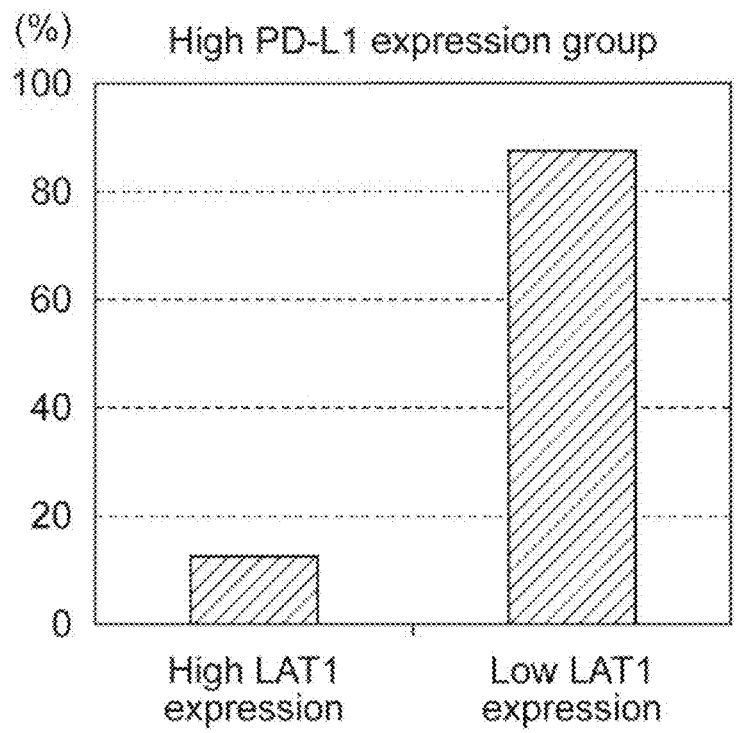
FIG. 11 is a pair of graphs showing the LAT1 expression (of all patients) in accordance with the PD-L1 expression levels. The upper graph (A) represents a high PD-L1 expression group and the lower graph (B) represents a low PD-L1 expression group.
Figure 11:
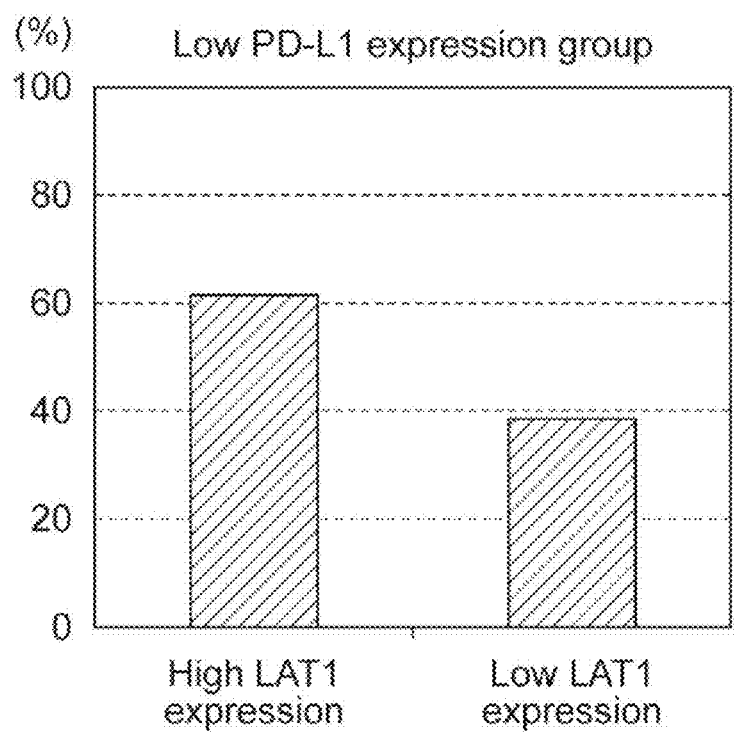
Figure 12:
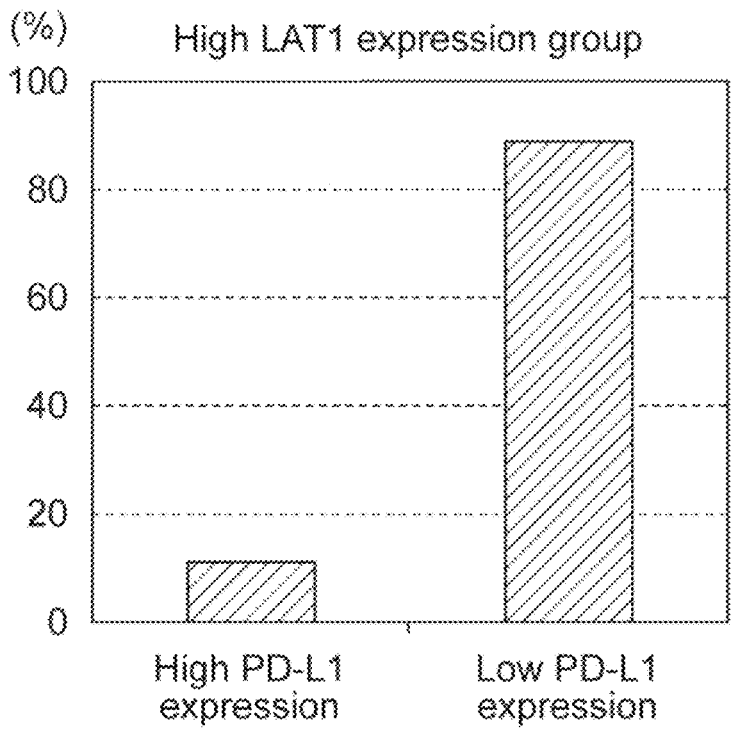
FIG. 12 is a pair of graphs showing PD-L1 expression (of all patients) in accordance with the LAT1 expression levels. The upper graph (A) represents a high LAT1 expression group and the lower graph (B) represents a low LAT1 expression group.
Figure 12:
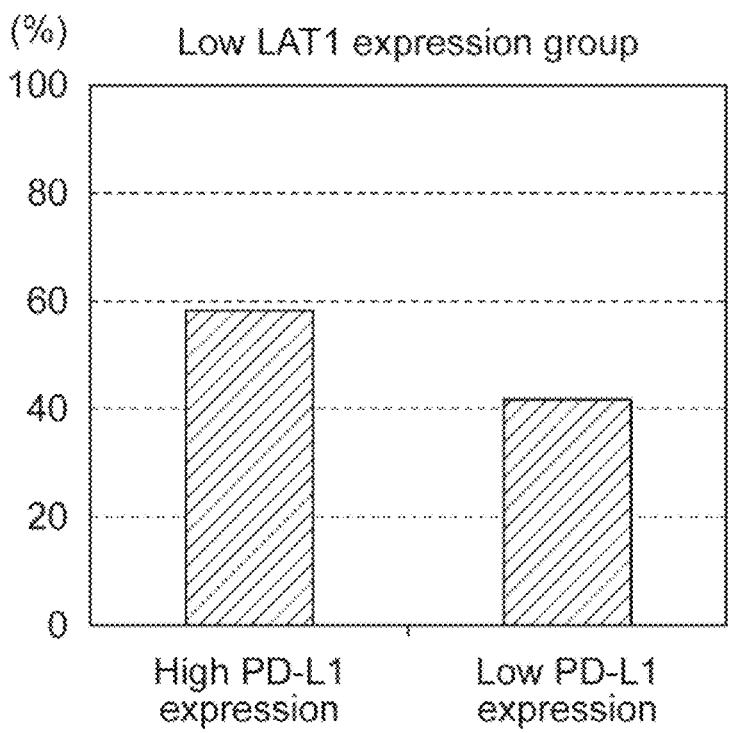

The results of expression levels of the two cancer markers in cancer tissue samples from 21 patients are shown in FIGS. 11 and 12. The high PD-L1 expression group had 8 of 21 patients (FIG. 11, upper panel), and the low expression group had 13 patients (FIG. 11, lower panel). Among the high PD-L1 expression group, the high LAT1 expression group had 1 patient and the low LAT1 expression group had 7 patients, and this difference was statistically significant (p=0.010). Among the low PD-L1 expression group, the high LAT1 expression group had 8 patients and the low LAT1 expression group had 5 patients, with no statistically significant difference observed (p=0.433).

The high LAT1 expression group had 9 of 21 patients (FIG. 12, upper panel), and the low expression group had 12 patients (FIG. 12, lower panel). Among the high LAT1 expression group, the high PD-L1 expression group had 1 patient and the low PD-L1 expression group had 8 patients, and this difference was statistically significant (p=0.003). Among the low LAT1 expression group, the high PD-L1 expression group had 7 patients and the low PD-L1 expression group had 5 patients, with no statistically significant difference observed (p=0.684).

From the foregoing results, negative correlation was found between the LAT1 expression and the PD-L1 expression in cancer tissues of non-small cell lung cancer patients.

As shown in the raw "tissue type" in Table 5, among total 21 patients with non-small cell lung cancer, 17 patients had lung adenocarcinoma and 4 patients had squamous cell carcinoma. The analysis of these 17 patients with lung adenocarcinoma revealed that all 7 patients with high PD-L1 expression had a low LAT1 expression (not shown). Moreover, all 8 patients with a high LAT1 expression had a low PD-L1 expression (not shown). Therefore, in cancer of either tissue type, negative correlation was found between the two cancer markers. The negative correlation between the LAT1 expression and the PD-L1 expression suggests the presence of unknown cross-talk between the markers in the cancer tissue.

(Test Example 2) Prediction of Response to Nivolumab in Non-Small Cell Lung Cancer (2)

Figure 13:
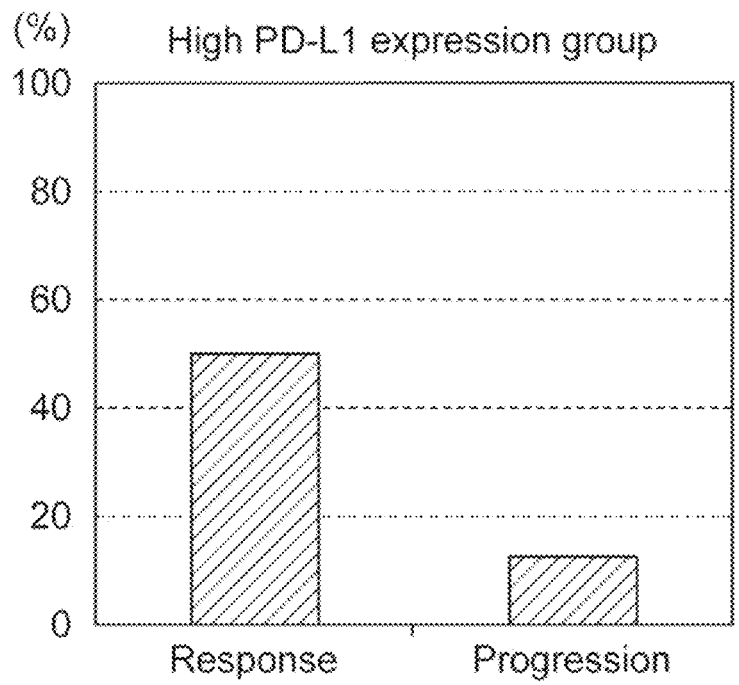
FIG. 13 is a pair of graphs showing the therapeutic benefit (of all patients) from nivolumab in accordance with the PD-L1 expression levels. The upper graph (A) represents a high PD-L1 expression group and the lower graph (B) represents a low PD-L1 expression group.
Figure 13:
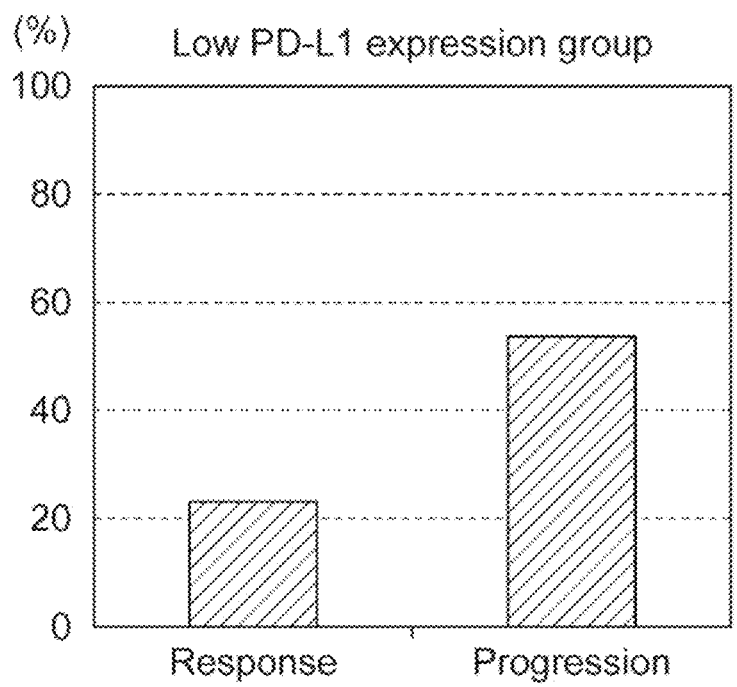
Figure 14:
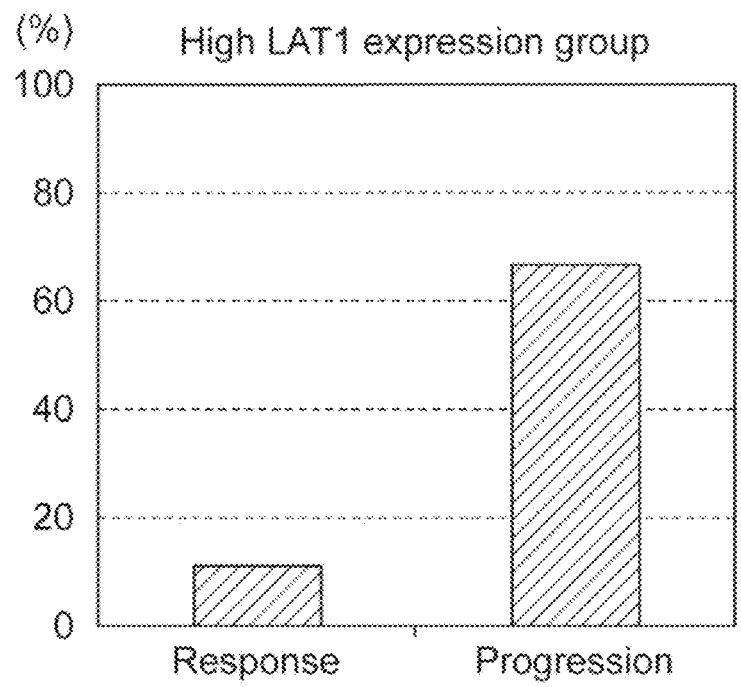
FIG. 14 is a pair of graphs showing the therapeutic benefit (of all patients) from nivolumab in accordance with the LAT1 expression levels. The upper graph (A) represents a high LAT1 expression group and the lower graph (B) represents a low LAT1 expression group.
Figure 14:
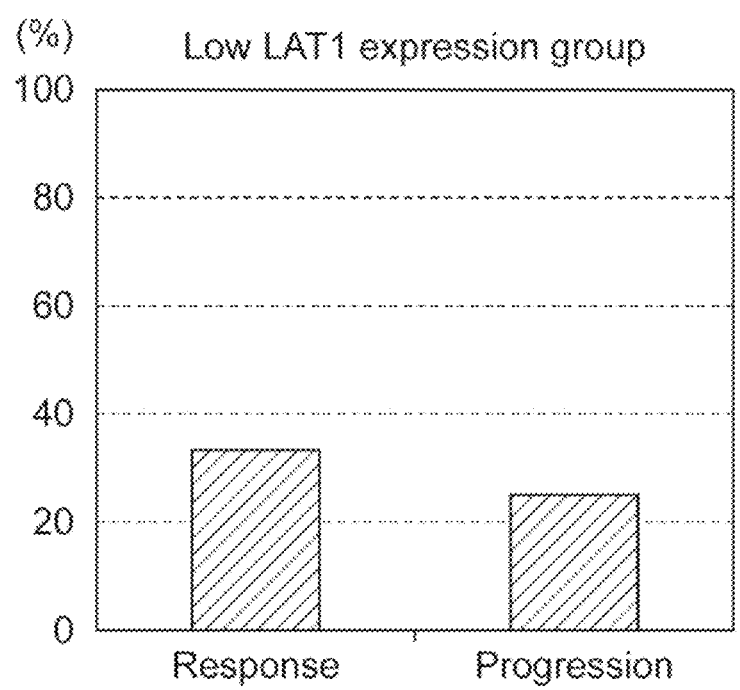

The possibility of predicting the response to nivolumab only based on the expression level of PD-L1 was examined. The two cancer markers were used as indicators. The results showing the response to nivolumab in cancer tissue samples from the 21 patients are shown in FIGS. 13 and 14. FIG. 13, upper panel shows the response of the PD-L1 high expression group, and FIG. 13, lower panel shows the response of the PD-L1 low expression group. The PD-L1 high expression group had 8 patients. Among them, 4 patients exhibited a response, 1 patient exhibited progression, and 3 patients were stable. On the other hand, the PD-L1 low expression group had 13 patients. Among them, 3 patients exhibited a response, 7 patients exhibited progression, and 3 patients were stable.

FIG. 14, upper panel shows the response of the high LAT1 expression group, and FIG. 14, lower panel shows the response of the low LAT1 expression group. The high LAT1 expression group had 9 patients. Among them, 1 patient exhibited a response, 6 patients exhibited progression, and 2 patients were stable. On the other hand, the low LAT1 expression group had 12 patients. Among them, 4 patients exhibited a response, 3 patients exhibited progression, and 5 patients were stable.

From the foregoing results, if a high response to nivolumab was predicted for a patient with a high PD-L1 expression and a low response to nivolumab was predicted for a patient with a low PD-L1 expression, then it would mean that the responses of 7 patients (4 patients with a response in the high PD-L1 expression group +3 patients with a response in the low PD-L1 expression group) out of 21 patients, thus only one-third of the total patients, were correctly predicted. Accordingly, although the expression of PD-L1 is necessary for the response to nivolumab as a major premise, the accuracy of the prediction would be 33% if the response to nivolumab was predicted only based on the expression level of PD-L1.

(Test Example 3) Prediction of Response to Nivolumab in Non-Small Cell Lung Cancer (3)

Figure 15:
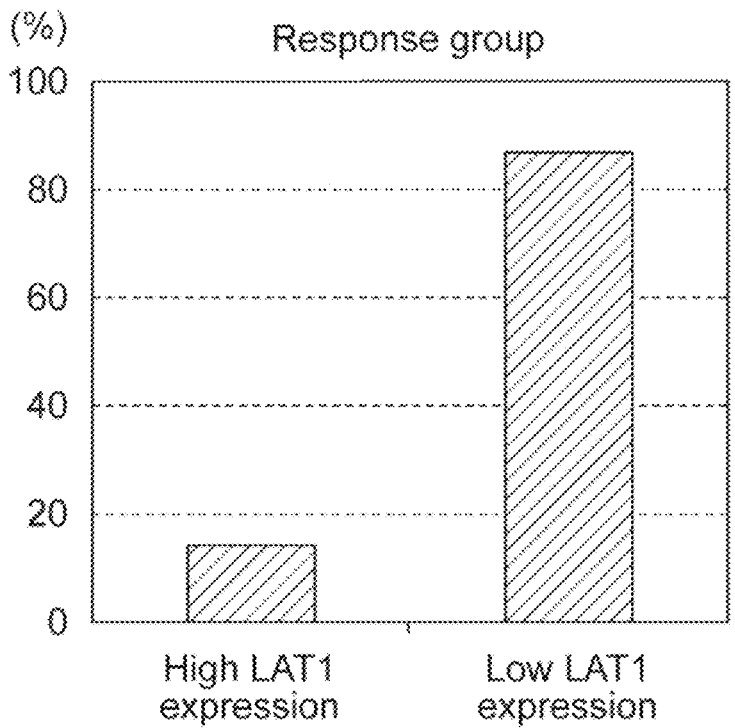
FIG. 15 is a pair of graphs showing the percentage of LAT1 expression in patients having response to nivolumab and in patients having progression with nivolumab. The upper graph (A) represents a response group and the lower graph (B) represents a progression group.
Figure 15:
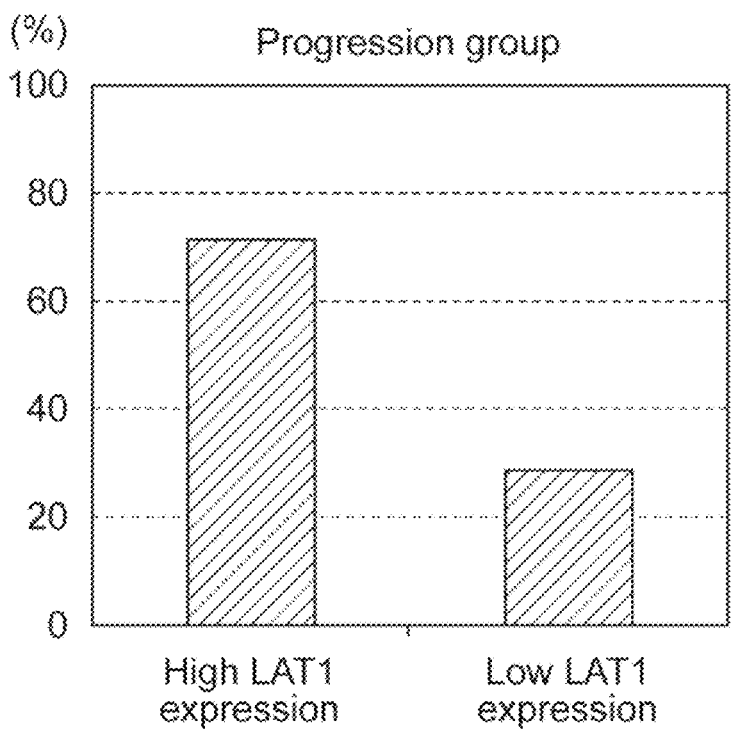

The possibility of predicting the response to nivolumab based on the expression levels of PD-L1 and LAT1 was examined. The results of response to nivolumab and the progression of the aforementioned 21 patients with non-small cell lung cancer are summarized in FIG. 15. FIG. 15, upper panel shows a response group, and FIG. 15, lower panel shows a progression group. Among 7 patients in the response group, the high LAT1 expression group had 1 patient and the low LAT1 expression group had 6 patients, with a statistically significant difference observed (p=0.029). Moreover, among 7 patients in the progression group, the high LAT1 expression group had 5 patients and the low LAT1 expression group had 2 patients, with no statistically significant difference observed.

The expression of PD-L1 itself was observed in all 21 patients, but 7 patients exhibited a response (response rate=33%) and 14 patients exhibited no response, and 7 patients, a half of the patients with no response exhibited progression. Since 6 patients out of the 7 patients with a response were of the low LAT1 expression group, the accuracy of prediction of the response rate would reach 85% (=6/7), by predicting the patients with a PD-L1 expression and a low LAT1 expression to have a high response to nivolumab. Meanwhile, from the aforementioned result, the accuracy of prediction of the progression rate based on the high expression of LAT1 would be 71% (=5/7).

(Test Example 4) Prediction of Prognosis for Patients Having Cancer Cells in which PD-L1 and LAT1 are Expressed in the Same Cell The prognoses of patients having cancer tissues of the PL-coexistent type in which the two cancer markers are present in the same cell, as already illustrated in FIGS. 3 and 10, are shown in Table 6. Since the two cancer markers are expressed in the same cell in the PL-coexistent type, the PL-coexistent type is considered to exhibit resistance to therapeutic agents specific to the molecule targets of respective markers. Since the detection of the PL-coexistent type tissue requires double staining of a single section, a high level of technique is necessary. It seems that this resistance to treatment can be overcome by the development of a novel therapy for target cancer cells.

Cancer tissues were collected from 2 of each of colorectal cancer, pancreatic cancer, lung cancer, and biliary cancer patients, and the expression of LAT1 and the expression of PD-L1 were examined by immunohistochemistry using an anti-LAT1 antibody and an anti-PD-L1 antibody. Whether there were cells expressing both PD-L1 and LAT1 was examined and summarized in Table 6.

As apparent from Table 6, it was found that patients comprising cells expressing both LAT1 and PD-L1 in cancer tissue have shorter survival years in comparison with patients comprising no cells expressing both LAT1 and PD-L1 in cancer tissue.

(Test Example 5) Mutual Effect of Knockdown of LAT1 and PD-L1

The suppression of mRNA expression of PD-L1 or LAT1 at the transcriptional level was attempted using siRNA. WiDr cells (derived from human colon-adenocarcinoma), SKN cells (human uterine leiomyosarcoma cells), and H520 cells (human pulmonary squamous cell carcinoma cells) were seeded in culture dishes. siRNA that suppresses the mRNA expression of PD-L1, siRNA that suppresses the mRNA expression of LAT1, or a control siRNA was introduced into cells. As the siRNA, Silencer (registered trademark) Select siRNAs of the Ambion (registered trademark) series from Thermo Fisher Scientific K.K. Specifically, siPD-L1 #2 (siRNA ID: s26548) set forth in SEQ ID NOs: 1 and 2 was used as the siRNA for suppressing the mRNA expression of PD-L1, siLAT1 #3 (siRNA ID: s15653) set forth in SEQ ID NOs: 3 and 4 was used as the siRNA for suppressing the mRNA expression of LAT1, and Silencer Select Negative control #2 (Cat #: 390847) was used as the control siRNA. Cells were collected 48 hours later, when the suppression effect on expression tends to be prominent, and mRNA expression levels of LAT1 and PD-L1 per cell were analyzed by quantitative PCR. The results are shown in Table 7.

TABLE 7

| | | Control si-RNA | si-PD-L1 | si-LAT1 |
|---|---|---|---|---|
| WiDr cells | LAT1 mRNA expression level | 1 | 5.01*** | 0.11 |
| | PD-L1 mRNA expression level | 1 | 0.46 | 1.82*** |
| SKN cells | LAT1 mRNA expression level | 1 | 1.52*** | 0.06 |
| | PD-L1 mRNA expression level | 1 | 0.24 | 1.04*** |
| H520 cells | LAT1 mRNA expression level | 1 | 2.29*** | 0.11 |
| | PD-L1 mRNA expression level | 1 | 0.37 | 0.82*** |

***p < 0.001, compared to the expression level indicated in the next column (si-PD-L1 or si-LAT1), n = 4

TABLE 6

| | | PD-L1 expression | LAT1 expression | PDL-1 & LAT1 expressions in the same cell | Survival years |
|---|---|---|---|---|---|
| Colorectal cancer | Patient 1 | Low | High | Absent | 16 years or more |
| | Patient 2 | High | High | Present | 8 years |
| Pancreatic cancer | Patient 3 | High | Low | Absent | 9 years or more |
| | Patient 4 | Low | High | Present | 1 year and 1 month |
| Lung cancer | Patient 5 | Low | High | Absent | 6 years or more |
| | Patient 6 | Low | High | Present | 3 years and 1 month |
| Biliary cancer | Patient 7 | Low | High | Absent | 8 years or more |
| | Patient 8 | Low | High | Present | 5 years and 3 months |

In Table 7, the mRNA expression levels per cell are expressed as relative values, with the mRNA expression level in the cells, to which the control siRNA was introduced, being 1. It was confirmed that the expressions of PD-L1 and LAT1 can be sufficiently suppressed by siRNAs corresponding to respective markers in all of WiDr cells, SKN cells, and H520 cells. Moreover, the suppression of PD-L1 expression increased the expression of LAT1, and the suppression of LAT1 increased the expression of PD-L1. These results suggested that suppression of expression of either one of PD-L1 and LAT1 increases the expression of the other one and that these proteins serve complementarily in cancer cells.

(Test Example 6) Change of PD-L1 Expression Level by JPH2O3

The LAT1 activity was suppressed using an inhibitor JPH2O3 instead of the gene suppression using siRNA, and it was examined whether results similar to Test Example 5 would be obtained. JPH2O3 is O-(5-amino-2-phenylbenzoxazol-7-yl)methyl-3,5-dichloro-L-tyrosine. HuccT1 cells (derived from human bile duct cancer) and OST cells (derived from human fibrosarcoma of bone) were seeded in culture dishes. After treatment with 30 μM of JPH2O3 (LAT1 selective inhibitor) for 24 hours, cells were collected and mRNA expression levels of PD-L1 were analyzed by quantitative PCR. The results are shown in Table 8.

TABLE 8

| | PD-L1 mRNA expression level | |
|---|---|---|
| | Control (without JPH203) | 24 hours treatment |
| HuccT1 cells | 1 | 12.26** |
| Ost cells | 1 | 2.79* |

*$P < 0.05$,
**$P < 0.01$ vs. control, $n = 4$

In Table 8, the mRNA expression levels per cell are expressed as relative values, with the expression level of the control that was not treated with JPH2O3 being 1. In both HuccT1 cells and OST cells, the expression of PD-L1 was increased. It was shown from this result that the selective inhibition of the LAT1 activity increases the expression of PD-L1. This result, together with the results of Test Example 5, supports that LAT1 and PD-L1 serve complementarily in cancer cells. Moreover, since the inhibition of LAT1 increased the expression of PD-L1, it is considered that the LAT1 inhibition therapy can increase the expression level of PD-L1 as well as reduce the expression level or activity of LAT1 in patients. In other words, it is considered that the expression level of PD-L1 in patients can be brought close to those in patients of the P-predominance type by the LAT1 inhibition therapy. As shown by the results of Test Example 1 and Test Example 3, the responses of patients having a high PD-L1 expression and a low LAT1 expression (patients of the P-predominant type) to nivolumab are high. Therefore, this Test Example suggests that the response of patients to an anti-PD-1 antibody or anti-PD-L1 antibody therapy can be increased by combining the anti-PD-1 antibody or anti-PD-L1 antibody therapy and a LAT1 inhibition therapy.

The invention claimed is:

1. A method for treating cancer in a subject, comprising: administering an anti-PD-1 antibody or an anti-PD-L1 antibody in combination with a LAT1 inhibitor to the subject, wherein the LAT1 inhibitor is O-(5-amino-2-phenylbenzoxazol-7-yl)methyl-3,5-dichloro-L-tyrosine or a pharmacologically acceptable salt thereof.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial  Sequence
<220> FEATURE:
<223> OTHER INFORMATION: siPD-L1#2 Sense
<220> FEATURE:
<221> NAME/KEY: misc_feature
<222> LOCATION: (1)..(19)
<223> OTHER INFORMATION: RNA fragment
<220> FEATURE:
<221> NAME/KEY: misc_feature
<222> LOCATION: (20)..(21)
<223> OTHER INFORMATION: DNA fragment

<400> SEQUENCE: 1
ggacucacuu gguaauucut t                                           21

<210> SEQ ID NO 2
<211> LENGTH: 21
<212> TYPE: DNA
<213> ORGANISM: Artificial  Sequence
<220> FEATURE:
<223> OTHER INFORMATION: siPD-L1#2 Antisense
<220> FEATURE:
<221> NAME/KEY: misc_feature
<222> LOCATION: (1)..(19)
<223> OTHER INFORMATION: RNA fragment
<220> FEATURE:
<221> NAME/KEY: misc_feature
<222> LOCATION: (20)..(21)
<223> OTHER INFORMATION: DNA fragment
```

```
<400> SEQUENCE: 2
agaauuacca agugagucct t                                              21

<210> SEQ ID NO 3
<211> LENGTH: 21
<212> TYPE: DNA
<213> ORGANISM: Artificial  Sequence
<220> FEATURE:
<223> OTHER INFORMATION: siLAT1#3 Sense
<220> FEATURE:
<221> NAME/KEY: misc_feature
<222> LOCATION: (1)..(19)
<223> OTHER INFORMATION: RNA fragment
<220> FEATURE:
<221> NAME/KEY: misc_feature
<222> LOCATION: (20)..(21)
<223> OTHER INFORMATION: DNA fragment

<400> SEQUENCE: 3
uguccaaucu agaucccaat t                                              21

<210> SEQ ID NO 4
<211> LENGTH: 21
<212> TYPE: DNA
<213> ORGANISM: Artificial  Sequence
<220> FEATURE:
<223> OTHER INFORMATION: siLAT1#3 Antisense
<220> FEATURE:
<221> NAME/KEY: misc_feature
<222> LOCATION: (1)..(19)
<223> OTHER INFORMATION: RNA fragment
<220> FEATURE:
<221> NAME/KEY: misc_feature
<222> LOCATION: (20)..(21)
<223> OTHER INFORMATION: DNA fragment

<400> SEQUENCE: 4
uugggaucua gauuggacac a                                              21
```